United States Patent
Mutti et al.

(10) Patent No.: US 10,402,980 B2
(45) Date of Patent: *Sep. 3, 2019

(54) IMAGING SYSTEM OBJECT RECOGNITION AND ASSESSMENT

(71) Applicant: Christopher M. Mutti, Hudson, MA (US)

(72) Inventors: Christopher M. Mutti, Hudson, MA (US); Daniel L. Lau, Lexington, KY (US); John P. Coates, Newtown, CT (US)

(73) Assignee: Christopher M. Mutti, Hudson, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/938,661

(22) Filed: Mar. 28, 2018

(65) Prior Publication Data

US 2018/0247417 A1  Aug. 30, 2018

Related U.S. Application Data

(62) Division of application No. 14/947,334, filed on Nov. 20, 2015, now Pat. No. 9,959,628.

(Continued)

(51) Int. Cl.
*G06T 7/13* (2017.01)
*G06T 7/62* (2017.01)

(Continued)

(52) U.S. Cl.
CPC .............. *G06T 7/13* (2017.01); *G01N 33/02* (2013.01); *G06K 9/00214* (2013.01);

(Continued)

(58) Field of Classification Search
CPC ... G06T 7/13; G06T 7/62; G06T 2207/20221; G06T 2207/20081; G06T 2207/10012;

(Continued)

(56) References Cited

U.S. PATENT DOCUMENTS 6,287,560 B1  9/2001  Fujii
6,585,516 B1  7/2003  Alabaster (Continued)

FOREIGN PATENT DOCUMENTS

EP  2 787 459 A1  10/2014
JP  2003232736  8/2003

(Continued)

OTHER PUBLICATIONS

Sadeghipoor et al, A novel compressive sensing approach to simultaneously acquire color and near-infrared images on a single sensor (Year: 2013).*

(Continued)

*Primary Examiner* — Shan E Elahi
(74) *Attorney, Agent, or Firm* — Morse, Barnes-Brown & Pendleton, P.C.; Sean D. Detweiler, Esq.

(57) ABSTRACT

A method and system for using one or more sensors configured to capture two-dimensional and/or three dimensional image data of one or more objects. In particular, the method and system combine one or more digital sensors with visible and near infrared illumination to capture visible and non-visible range spectral image data for one or more objects. The captured spectral image data can be used to separate and identify the one or more objects. Additionally, the three-dimensional image data can be used to determine a volume for each of the one or more objects. The identification and volumetric data for one or more objects can be used individually or in combination to obtain characteristics about the objects. The method and system provide the user with the ability to capture images of one or more objects and obtain related characteristics or information about each of the one or more objects.

21 Claims, 13 Drawing Sheets

Related U.S. Application Data

(60) Provisional application No. 62/082,795, filed on Nov. 21, 2014.

(51) Int. Cl.

| | | |
|---|---|---|
| *G01N 33/02* | (2006.01) | |
| *G06K 9/00* | (2006.01) | |
| *G06K 9/20* | (2006.01) | |
| *G06K 9/22* | (2006.01) | |
| *G06K 9/46* | (2006.01) | |
| *G06K 9/62* | (2006.01) | |
| *H04N 13/254* | (2018.01) | |

(52) U.S. Cl.
CPC ..... *G06K 9/00671* (2013.01); *G06K 9/00771* (2013.01); *G06K 9/2018* (2013.01); *G06K 9/2036* (2013.01); *G06K 9/228* (2013.01); *G06K 9/4604* (2013.01); *G06K 9/6293* (2013.01); *G06T 7/62* (2017.01); *G06K 2009/4657* (2013.01); *G06K 2209/17* (2013.01); *G06T 2207/10012* (2013.01); *G06T 2207/10024* (2013.01); *G06T 2207/10028* (2013.01); *G06T 2207/10048* (2013.01); *G06T 2207/20076* (2013.01); *G06T 2207/20081* (2013.01); *G06T 2207/20221* (2013.01); *G06T 2207/30128* (2013.01); *H04N 13/254* (2018.05)

(58) Field of Classification Search
CPC . G06T 2207/10024; G06T 2207/30128; G06T 2207/20076; G06T 2207/10028; G06T 2207/10048; H04N 13/254
USPC .......................................................... 348/143
See application file for complete search history.

(56) References Cited

U.S. PATENT DOCUMENTS

| | | | |
|---|---|---|---|
| 8,139,141 B2 | 3/2012 | Bamji et al. | |
| 8,285,015 B2 | 10/2012 | Demos | |
| 8,363,913 B2 | 1/2013 | Boushey et al. | |
| 8,605,952 B2 | 12/2013 | Boushey et al. | |
| 8,690,578 B1 | 4/2014 | Nusbaum et al. | |
| 8,862,181 B1* | 10/2014 | Cope | G06Q 20/327 455/39 |
| 9,424,495 B1 | 8/2016 | Trevino | |
| 9,959,628 B2 | 5/2018 | Mutti et al. | |
| 2003/0076983 A1* | 4/2003 | Cox | G06K 9/00 382/110 |
| 2004/0081621 A1 | 4/2004 | Arndt et al. | |
| 2004/0211903 A1* | 10/2004 | Bynum | G01N 21/4795 250/341.1 |
| 2006/0036395 A1 | 2/2006 | Shaya et al. | |
| 2006/0200480 A1* | 9/2006 | Harris | G06Q 30/06 |
| 2007/0050058 A1 | 3/2007 | Zuziak et al. | |
| 2007/0090186 A1* | 4/2007 | Lawrence | G06Q 30/02 235/383 |
| 2007/0116808 A1 | 5/2007 | Gordon | |
| 2007/0218174 A1 | 9/2007 | Hanamatsu et al. | |
| 2008/0174777 A1 | 7/2008 | Carron | |
| 2009/0184247 A1 | 7/2009 | Shimazu et al. | |
| 2010/0000960 A1 | 1/2010 | Anderson | |
| 2010/0062196 A1 | 3/2010 | Bezek et al. | |
| 2010/0111383 A1 | 5/2010 | Boushey et al. | |
| 2010/0207877 A1* | 8/2010 | Woodard | G06F 3/013 345/156 |
| 2010/0292330 A1* | 11/2010 | Pan | A61K 31/198 514/560 |
| 2010/0299074 A1 | 11/2010 | Chang et al. | |
| 2010/0310750 A1* | 12/2010 | She | A23K 40/20 426/578 |
| 2011/0050880 A1* | 3/2011 | Bourg, Jr. | G01N 21/8851 348/89 |
| 2011/0182477 A1 | 7/2011 | Tamrakar et al. | |
| 2011/0192351 A1 | 8/2011 | Jackson | |
| 2011/0236862 A1 | 9/2011 | Culver et al. | |
| 2011/0292181 A1 | 12/2011 | Acharya et al. | |
| 2012/0005222 A1 | 1/2012 | Bhagwan et al. | |
| 2012/0053426 A1 | 3/2012 | Webster et al. | |
| 2012/0071765 A1 | 3/2012 | Chinnock | |
| 2012/0096405 A1 | 4/2012 | Dongkyu | |
| 2012/0135384 A1 | 5/2012 | Nakao | |
| 2012/0170801 A1 | 7/2012 | DeOliveira et al. | |
| 2012/0179665 A1 | 7/2012 | Baarman et al. | |
| 2012/0299920 A1* | 11/2012 | Coombe | G06T 19/00 345/423 |
| 2013/0105565 A1 | 5/2013 | Kamprath | |
| 2013/0216982 A1 | 8/2013 | Bennett et al. | |
| 2013/0273509 A1 | 10/2013 | Mutti | |
| 2013/0329101 A1 | 12/2013 | Choi et al. | |
| 2013/0335418 A1* | 12/2013 | Kim | G06Q 10/00 345/424 |
| 2014/0147829 A1 | 5/2014 | Jerauld | |
| 2014/0170608 A1 | 6/2014 | Ting et al. | |
| 2014/0218538 A1 | 8/2014 | Choi | |
| 2014/0231626 A1 | 8/2014 | Nelson et al. | |
| 2014/0315161 A1 | 10/2014 | Sako et al. | |
| 2014/0351073 A1 | 11/2014 | Murphy et al. | |
| 2015/0035961 A1 | 2/2015 | Chen et al. | |
| 2015/0036138 A1 | 2/2015 | Watson et al. | |
| 2015/0109451 A1 | 4/2015 | Dhankhar | |
| 2015/0304612 A1 | 10/2015 | Richards et al. | |
| 2016/0035248 A1 | 2/2016 | Gibbs | |
| 2016/0063734 A1 | 3/2016 | Divakaran et al. | |
| 2016/0163037 A1 | 6/2016 | Dehais et al. | |
| 2017/0069225 A1 | 3/2017 | Ortiz et al. | |

FOREIGN PATENT DOCUMENTS

| | | |
|---|---|---|
| WO | WO 2012/094569 | 7/2012 |
| WO | WO 2012/115297 | 8/2012 |
| WO | WO 2012/155104 | 11/2012 |
| WO | WO 2013/065035 | 5/2013 |
| WO | WO 2016/081831 | 5/2016 |

OTHER PUBLICATIONS

Kim, "An Approximate Inverse Recipe Method With Application to Automatic Food Analysis," pp. 1-8 (2014).

Nabi, et al., "Smart Dietary Monitoring System," *IEEE International Symposium on Nanoelectronic and Information Systems*, pp. 207-212, (2015).

Zhou, et al., "Smart Table Surface: A Novel Approach to Pervasive Dining Monitoring," *IEEE International Symposium on Pervasive Computing and Communications*, pp. 155-162, (2015).

Zhu, et al., "The Use of Mobile Devices in Aiding Dietary Assessment and Evaluation", *IEEE Journal of Selected Topics in Signal Processing*, 4(4):756-766, (Aug. 2010).

International Search Report and Written Opinion for PCT Application No. PCT/US2015/061849, dated Apr. 11, 2016.

European Search Report for European Application No. EP 14162959, dated Jul. 30, 2014.

Non-Final Office Action for U.S. Appl. No. 13/857,427, dated Sep. 22, 2016.

Final Office Action for U.S. Appl. No. 13/857,427, dated Oct. 19, 2017.

Notice of Allowance for U.S. Appl. No. 14/947,334, dated Jan. 22, 2018.

\* cited by examiner

Nutritional Label Entire Meal

Nutrition Facts

Lunch Serving

Serving size 1 plate

Amount per this 3D image

Calories 626

%DV*

28% Total Fat g 18
   53% Saturated Fat g 11
      Trans Fat g 1
57% Cholesterol mg 172
34% Sodium mg 819
14% Total Carbs g 43
   23% Dietary Fiber g 6
      Sugars g 7
      Protein g 69

0% Vitamin A mcg 0
66% Vitamin C mg 40
261% Vitamin D mcg 26
12% Calcium mg 121
27% Iron mg 5
30% Potassium mg 1394

*Daily Values (DV) percent based on following quantities:
Total Fat 65g
Saturated Fat 20g
Cholesterol 300mg
Sodium 2400mg
Carbs 300g
Dietary Fiber 25g
Vitamin A 900 mcg
Vitamin C 60 mg
Vitamin D 10 mcg
Calcium 1300 mg
Potassium 4700 mg

IMAGING SYSTEM OBJECT RECOGNITION AND ASSESSMENT

CROSS-REFERENCE TO RELATED APPLICATION(S)

This application is a divisional of co-pending U.S. application Ser. No. 14/947,334 filed Nov. 20, 2015, which claims priority to Provisional Application No. 62/082,795, filed Nov. 21, 2014, for all subject matter common to said applications. The disclosures of said applications are hereby incorporated by reference in their entirety.

FIELD OF THE INVENTION

The present invention relates generally to a system which combines one or more sensors configured to capture two-dimensional and/or three dimensional image data of one or more objects. In particular, the present invention relates to a system configured to capture and export the spectral image data and dimensional data of one or more objects, such as for example food items, to a network based application. The network based application portion of the system draws upon a plurality of databases of algorithms and tabulated data to facilitate characteristics of the one or more objects, and implementation of comprehensive programs for users to automatically track and monitor desired variables, features, and characteristics of the one or more objects.

BACKGROUND

Generally, people have been using a multitude of different methods and devices to track dietary food consumption and fitness. These methodologies include systems for counting calories, tracking points, excluding or limiting certain types of foods, etc. These systems can also include fitness tracking for estimating how many calories the user may have burned in relation in estimated caloric intake. Overall, the widespread use of smartphones, tablets, and other mobile devices has revolutionized the way in which many people monitor and guide their food consumption habits.

However, these devices, systems, applications, and methodologies experience several shortcomings. In particular, the current diet monitoring technologies experience several shortcomings based in part on shortcomings in the object imaging and characterization technologies. The most popular food related tracking and recording applications are intended for use with a smartphone, allowing users to download the application, set up a user account in which the user enters their goals for weight loss, amount of exercise, macronutrient intake, blood pressure, sleep patterns, etc. Conventional applications require the user to manually log their food intake and exercise through self-reporting based on the selections from a network database of foods and associated values. Using the manually reported information, diet monitoring applications typically output nutritional information based on the user input. Many users find the manual entry of foods difficult, bothersome, and confusing, which leads to users failing to use the application consistently or correctly for long periods of time and in turn reducing the effectiveness of such existing technology.

Additionally, several handheld consumer spectrometer devices, which use spectrometry to analyze the chemical composition of food (primarily to identify allergens) are more common. However these handheld spectrometer devices are not integrated with any means of automatically determining the volume of the portions, or to automatically separate and isolate the various foods on a plate to automatically analyze an entire meal. The spectrometers require users to manually enter their dietary intake and exercise to monitor their calorie and nutrient intake. Additionally, the handheld spectrometers represent another device for users carry around for use when they need to capture chemical compositions of food items within their meals, in addition to other common devices such as smartphones. Finally, the handheld consumer spectrometer devices are expensive. There is a need for system that provides a comprehensive means for the user to capture image data of one or more objects, such as food items, and automatically assess characteristics of the one or more objects and use the determined characteristics to automatically implement desired processes, such as the obtaining, tracking and monitoring of caloric and nutrient intake, in a more cost effective manner that leverages pre-existing user devices such as smartphones in a more robust manner.

SUMMARY

There is a need for an imaging system that allows a user to capture an image of one or more objects, and instantly correlate the captured image to data recognizing the objects in the image and calculating, determining, or obtaining additional useful information about the objects. For purposes of the present application, the imaging system implementation will be described within a use case of food item analysis, including providing a user of the system with the ability to capture images of food items and obtain caloric and nutrient related characteristics or information (e.g., actual food weights), so as to enable dietary management. However, the technology of the present invention can be utilized in fields outside of the food management field, as would be appreciated by those of skill in the art.

In the specific implementation example of capturing food item characteristics, the system of the present invention enables a user to capture an image of one or more food items the user is about to consume or purchase and instantly obtain a display on their device of the nutritional facts and ingredient labels (e.g., similar to the standard Food and Drug Administration (FDA) labels) displaying the actual weight, calories, cholesterol, sodium, carbohydrates, sugars, and other nutritional values of the food, and then be recording such information in, for example, a user's account.

The system of the present invention is directed toward further solutions to address these needs, in addition to having other desirable characteristics. Specifically, the present invention is a comprehensive and automated system that brings together the functionality of a 3D scanner and a two-dimensional and/or three dimensional digital imaging sensor to capture data needed for the identification and characterization of at least one object, such as a food item, within a field of view. The system of the present invention offers an extensive suite of cloud and/or network based-resources to leverage the data captured by the system to gather, calculate, synthesize, and display information to the user regarding the one or more objects, such as nutritive values of the scanned food items in the example implementation. The system of the present invention enables automatic monitoring of food and nutrient intake. The system of the present invention may be used to gather information from spectral signatures, and two-dimensional or three dimensional digital camera images, and 3D scans of objects such as food items, and use that information in conjunction with a network based application in communication with a plurality of databases of algorithms and tabulated object data to collect, store, and display information to a user, and in the food item example to provide such information related to a user's eating habits and food intake.

In accordance with an illustrative embodiment of the present invention, a method for automated detection and processing of a plate of food for nutritional values is provided. The method includes detecting, by at least one sensor, edges of the plate of food based on a depth of the plate of food in relation to other objects in a field of view, and capturing, by the at least one sensor, a three-dimensional model of the plate of food. The method also includes capturing, by the at least one sensor, image data for the plate of food, the image data including a visible light image and at least one near-infrared (NIR) image of the plate of food and transforming, by a processor, the image data into a composite image, the composite image mimicking a single image taken by a single sensor. The method further includes identifying, by a processor, a food item that corresponds to the composite image, transforming, by a processor, the three-dimensional model of the identified food item into a volume for the identified food item, and calculating, by a processor, dietary information of the identified food item based on the volume of the food item.

In accordance with aspects of the present invention, the method can include determining an initial volume of the identified food item, determining a final volume of the identified food item, and calculating a change in volume of the identified food item based on a difference of the initial volume of the identified food item and the final volume of the identified food item.

In accordance with aspects of the present invention, the method can include obtaining, from a database, dietary information for the identified food item and calculating dietary content of the change in volume of the identified food item.

In accordance with aspects of the present invention, the method can include illuminating the plate of food by an LED array and obtaining reflected image data at wavelengths of 745 nm, 810 nm, 940 nm, 970 nm, and/or 1050 nm, and correlating the reflected image data to characteristic food elements.

In accordance with aspects of the present invention, the volume and a weight for the identified food item can be calculated in relation to the visible light image and the at least one near-infrared (NIR) image.

In accordance with an illustrative embodiment of the present invention, a method for automated detection and processing of one or more objects in a target area is provided. The method includes detecting, by at least one sensor, edges of the target area based on a depth of the target area in relation to other objects in a field of view and capturing, by the at least one sensor, a three-dimensional model of the one or more objects within the target area. The method also includes capturing, by the at least one sensor, image data for the one or more objects, the image data including an RGB separated elements or vectors from visible image and a plurality of near infrared vectors for specific wavelengths extracted from the image data of reflected light from the one or more objects and transforming, by an image processing module, the image data into a composite image, the composite image mimicking a single image taken by a single sensor. The method further includes identifying, by the image processing module, at least one object of the one or more objects that corresponds to color pixels of the composite image and determining, by the image processing module, a volume of space for each pixel in the three-dimensional model based on a depth of pixels. The method also includes transforming, by the image processing module, the volume of space for each pixel for each identified at least one object into a volumetric value for the at least one object and summing, by the image processing module, volumetric values of each of the color pixels of the identified at least one object in the composite image to calculate a total volume of the at least one object.

In accordance with an illustrative embodiment of the present invention, a system is provided. The system includes a digital camera. The digital camera includes at least one image sensor, the digital camera configured to transform captured visible light in a spectrum range and Near Infrared (NIR) light in a spectrum range into captured light voltage, at least one image processing module that transforms the captured light voltage into three-dimensional (3D) image data, and a recording device that records the 3D image data. The digital camera captures and records at least two different and non-overlapping subsets of light spectrum ranges within the NIR spectrum range and does not record gaps of light spectrum ranges between the non-overlapping subsets of light spectrum ranges. The system also includes an image processing engine. The image processing engine is configured to analyze the captured and recorded captured light voltage to identify one or more objects, determine volumetric data for the one or more objects at a given period of time based on the recorded three-dimensional image data, and obtain characteristic information data, from one or more databases, for the identified one or more objects. The system further includes a display device for outputting the volumetric data and the characteristic information data for the one or more objects.

In accordance with aspects of the present invention, the visible light can be captured in the spectrum range of 400 nm to 700 nm and the NIR light can be captured in the spectrum range of 700 nm to 1050 nm.

In accordance with aspects of the present invention, the at least one image sensor can further include a three-dimensional scanner configured to capture three-dimensional point cloud data of the one or more objects, a digital NIR camera with a visible light blocking filter configured to capture light voltage for the one or more objects, and an RGB digital camera configured to capture two-dimensional or three-dimensional image data for the one or more objects. The digital NIR camera captures a series of two or more images for the at least two different and non-overlapping subsets of light spectrum ranges by cycling one at a time through an array of NIR LEDs.

In accordance with aspects of the present invention, the captured light voltage is used to identify one or more sub-objects of the one or more objects. The identified one or more sub-objects of the one or more objects can be separated and the characteristic information data for each of the one or more sub-objects can be obtained from the one or more databases.

In accordance with aspects of the present invention, the artificial intelligence engine can identify at least one predefined primitive and triggers the RGB digital camera and the digital NIR camera directed at the at least one predefined primitive.

In accordance with aspects of the present invention, the at least one image processing module can be configured to use three-dimensional point cloud data of the one or more objects to determine a range from the at least one image sensor to the one or more objects, to determine a surface area of the one or more objects, and calculate a size and shape of the one or more objects using the time of flight and the surface area without requiring use of a fiduciary reference token. The time of flight and the surface area of the one or more objects can be determined by calculating a number of pixels in a field of view of the three-dimensional point cloud data.

In accordance with an illustrative embodiment of the present invention, a system for automated determination of an object is provided. The system includes an array of Near Infrared (NIR) light emitting diodes (LEDs), the array containing LEDS of at least two different wavelengths, a three-dimensional scanner configured to capture a three-dimensional image of the object, a digital RGB camera configured to capture two-dimensional and/or three-dimensional visible image data of the object, and a digital NIR camera configured to capture NIR image data of the object. The array of NIR LEDs emit controlled light in predetermined spectrum ranges, and the three-dimensional scanner captures three-dimensional image data of the object, the digital RGB camera captures the two-dimensional visible image data of the object, and the digital NIR camera captures a series of NIR data sets while simultaneously triggering a unique LED wavelength for each NIR data set of the object. The three-dimensional image data of the object, the two-dimensional and/or three-dimensional visible image data of the object, and the NIR data of the object are transformed by the system into a characteristic correlated definition in terms of composition of the object and volume of the object.

In accordance with an illustrative embodiment of the present invention, a system is provided. The system includes a digital camera. The digital camera includes at least one image sensor, the digital camera configured to transform captured visible light in a spectrum range and Near Infrared (NIR) light in a spectrum range into captured image data. The system also includes at least one three-dimensional image scanner configured to capture three-dimensional image data; wherein the digital camera captures at least two different and non-overlapping subsets of light spectrum ranges within the NIR spectrum range and does not capture light in gaps of light spectrum ranges between the non-overlapping subsets of light spectrum ranges.

In accordance with aspects of the present invention, the at least one image sensor can further include a three-dimensional scanner sensor configured to capture the three-dimensional image data, a digital RGB camera sensor configured to capture two-dimensional visible light image data, and a digital NIR camera sensor with a visible light blocking filter configured to capture two-dimensional and/or three-dimensional NIR image data. In some implementations, the at least one image processing module can be configured to transform image data from the three-dimensional scanner sensor, the digital RGB camera sensor, and the digital NIR camera sensor into a representative set of image data originating from a single sensor. In some implementations, the system can also include at least two light source devices configured to produce non-overlapping spectrums. The at least one image sensor captures the at least two different and non-overlapping subsets of light spectrum ranges within the NIR spectrum range for each of the at least two light source devices by capturing image data during activation of each individual light source of the at least two light source devices.

In accordance with aspects of the present invention, the at least one image processing module can be configured to capture an N set of image data. The N set of image data includes image data for a visible light image capture and image data from N−1 NIR image captures. The at least one image processing module can also be configured to capture ambient image data with all of the at least two light source devices set to off and subtract the ambient image data from the N set of image data.

In accordance with aspects of the present invention, the digital camera further includes a lens, a sensor, and a three-dimensional microprocessor and the at least one sensor can capture the three-dimensional image data using at least one of stereovision, time of flight, and structured light.

In accordance with aspects of the present invention, the at least one image sensor can further include at least a micro electrical mechanical spectrometry chipset, an infrared (IR) source, a plurality of condenser lenses, a slit, an IR band pass filter, a diffraction grating, a digital micro-mirror device, a detector, and microprocessor. The system can further include wired and wireless connection devices configured to communicate data over a network.

In accordance with aspects of the present invention, the digital camera can be configured to transform captured ultraviolet (UV) light in a spectrum range of 100 nm to 400 nm into captured light voltage. In some implementations, the visible light can be captured in the spectrum range of 400 nm to 700 nm and the NIR light can be captured in the spectrum range of 700 nm to 1050 nm.

In accordance with an illustrative embodiment of the present invention, an object assessment system is provided. The system can include an imaging sensor application program interface (API) configured to capture and store visual spectral range image data and near infrared spectral image data of one or more objects. The system can also include a three-dimensional scanner API configured to capture and store three dimensional image data of the one or more objects. The system can further include a visual comparison API configured to identify the one or more objects based on the captured visual spectral range image data and near infrared spectral image data. The system can also include an auto-segmentation API configured to separate each of the one or more objects based on the identification by the visual comparison API and calculate a volume for each of the separate one or more objects based on the three-dimensional image data.

In accordance with aspects of the present invention, the one or more objects can be one or more food items in a meal. The system can further include a volume and weight API configured to cross-reference the identified one or more objects with a remote database to determine nutritive values of the one or more objects. The system can also include a nutritive value output API configured to output nutritional information for each of the one or more objects based on the nutritive values.

In accordance with aspects of the present invention, the visual comparison API can compare the visual spectral range image data and near infrared spectral image data to predetermined image data values stored in a database.

In accordance with aspects of the present invention, the system can further include a bar code and optical character recognition API configured to analyze a universal product code (UPC) or list of characters to obtain addition information for the system.

In accordance with an illustrative embodiment of the present invention, a method is provided. The method includes capturing, by a three-dimensional image scanner, a three-dimensional image. The method also includes determining a range between the three-dimensional image scanner and one or more objects based on data from the three-dimensional image. The method further includes determining, by an image processing module, a volume of each of the one or more objects based on the range and the data from the three-dimensional image. The method also includes capturing, by an RGB camera module, a visible light image and capturing, by a near infrared (NIR) camera module, a sequence of NIR images while simultaneously triggering a unique LED wavelength for each captured NIR image. The method further includes analyzing, by an artificial intelligence module, the captured visible light image and the sequence of NIR images to identify each unique object of the one or more objects and determining additional characteristics about the one or more objects based on the identified one or more objects and the volume of each of the one or more objects.

In accordance with an illustrative embodiment of the present invention, an imaging system for object recognition and assessment as described herein, and equivalents, in any operable combination, is provided.

In accordance with an illustrative embodiment of the present invention, a method of recognizing and assessing objects as described herein, and equivalents, in any operable combination of steps, is provided.

BRIEF DESCRIPTION OF THE FIGURES

These and other characteristics of the present invention will be more fully understood by reference to the following detailed description in conjunction with the attached drawings, in which:

FIGS. 3a, 3b, 3c, and 3d illustrate example housings for system, in accordance with aspects of the present invention;

FIGS. 10a and 10b are depictions of nutritional information resulting from scanning the meal in FIG. 9, in accordance with aspects of the invention.

DETAILED DESCRIPTION

Figure 1:
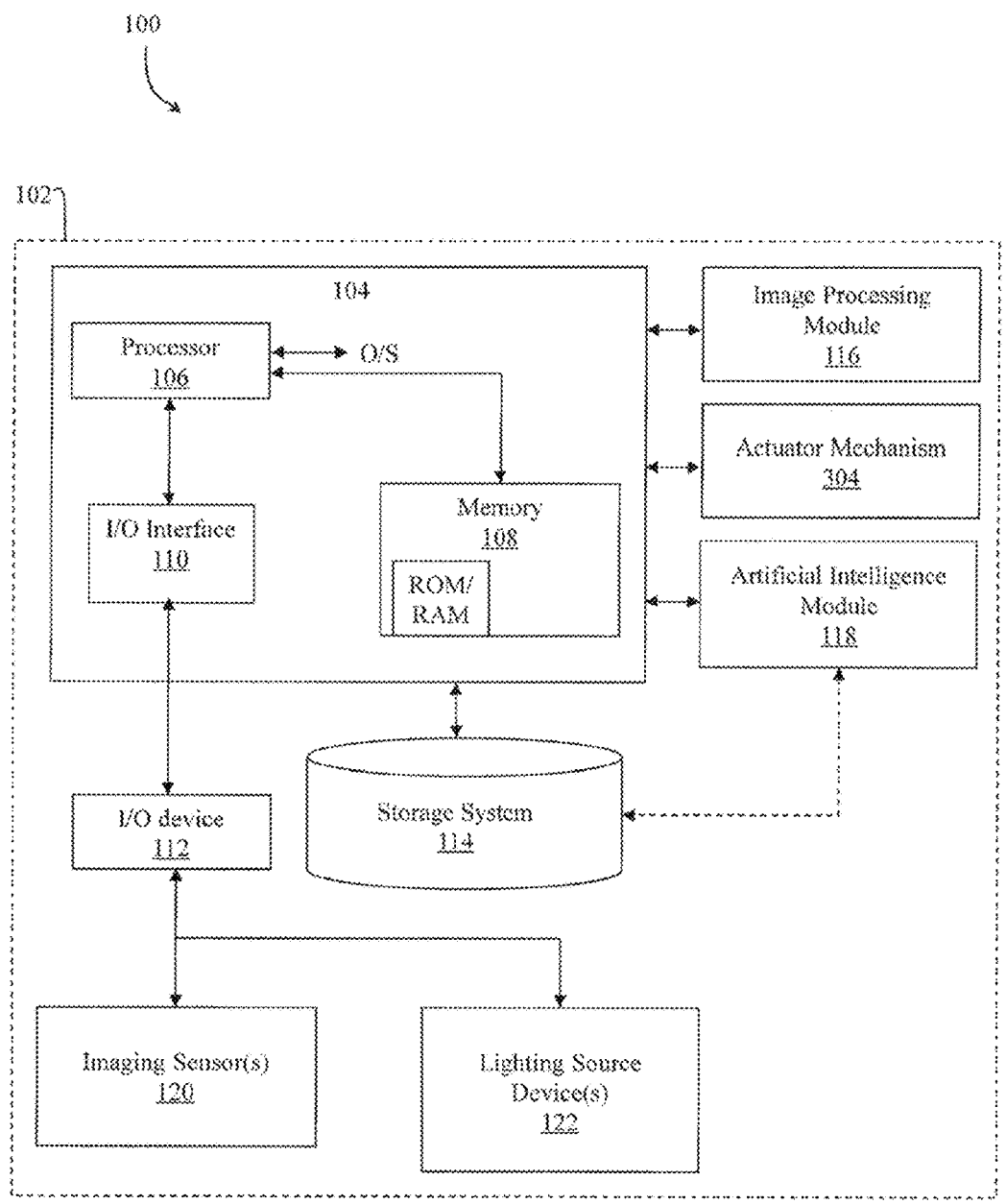
FIG. 1 depicts a system for capturing and automatically determining characteristics of one or more objects, in accordance with the present invention.

An illustrative embodiment of the present invention relates to a system for imaging and determining characteristics of (e.g., identifying, analyzing, etc.) one or more objects at the same time and obtaining additional information about the one or more objects based at least in part on identification and volume determinations of the one or more objects without requiring use of a fiduciary object as a reference for determining scale, or the like. In particular, the present invention relates to a system using a device utilizing both visible and near infrared three-dimensional imaging for identifying and analyzing one or more objects, such as food items, within a field of view, and determining the volume and other characteristics of those objects, such as caloric and nutritional values for food items. The technology of the present invention enables multiple objects (such as an entire plate of food) to be located within a single field of view, if desired, and the processes of the present invention to be implemented to image and determine characteristics of those multiple objects. The present invention utilizes a single two-dimensional and three dimensional sensor or combination of sensors with one or more light sources to capture image data (or captured light voltage) for the one or more objects using a vast portion of the electromagnetic spectrum. The system of the present invention provides a unique combination of different sensory methods that are brought together through the use of sensor fusion technology. Specifically, the two-dimensional and three-dimensional sensor(s) are capable of capturing image data over electromagnetic wavelengths that cover the visible spectral region of about 400 nm to 700 nm and the non-visible near infrared spectral region of about 700 nm to 1050 nm. The identification of the one or more objects can be obtained by combining image analysis of the image data in the visible spectral range and spectral analysis of the image data in the near infrared spectral region. The spectral analysis can be performed on the data captured by the two-dimensional and three-dimensional sensor(s) to derive spectral signatures for the one or more objects within a captured image and utilize the spectral signatures to identify the one or more objects within a captured image.

Additionally, the two-dimensional and three-dimensional sensor(s) can capture three-dimensional data of the object and use the captured three-dimensional data to determine an estimated volume of the one or more objects. The combined spectral signatures and three-dimensional volumetric data can be captured and analyzed to automatically determine various characteristics of the target one or more objects. In an example embodiment, the combined visual image data, spectral signature data, and three-dimensional volumetric data of food items can be used to automatically determine actual food weights, and separate and isolate various foods on a plate, and determine a standard nutritional facts label for each food item of the captured meal image. Additionally, the three-dimensional data can be used to determine a difference in volumetric data at different periods of time. The difference in volumetric data can be applied for various useful purposes, including for example determining an amount of food items consumer by a user and the associated nutritional facts for the amount of consumed food items.

When utilized in combination with the dietary system of the present invention, the combined two-dimensional visual image data, spectral signature image data, and three-dimensional volumetric data can be used to automatically track a user's nutritional intake and provide additional information for the user to assist in meeting nutritional goals. One implementation of automatic nutritional tracking requires the user capturing image data and three-dimensional volumetric data before eating a meal and again after eating the meal. The system of the present invention can use the image data and three-dimensional volumetric data to automatically identify the food items within the meal, separate the individual types of food items, determine an initial food volume for each type and a final food volume for each type, and calculate the nutritional values of the consumed portion of the meal (e.g., the nutritional values of the difference of the initial food volume and the final food volume). This process provides the user with all the nutritional information for the food consumed while only requiring the user to capture before and after image data for a meal without requiring the use of a fiduciary item or manually input data from the user. The use of the two-dimensional and three-dimensional sensor(s) and unconventional steps involved in object assessment system/dietary tracking system provides a unique improvement to the object recognition technologies. In particular, the unconventional steps of using data captured by image sensors to identify individual items within a group of items, determining volumetric data for each of the individually identified items, and determining additional characteristic information about the identified items based on the identification and the volume is an improvement to traditional object recognition technologies. As would be appreciated by one skilled in the art, the examples of tracking nutritional information for identified food items is intended to be for exemplary purposes only and the present invention can be utilized to identify and calculate volumetric information and other characteristic information for various types of objects for a particular purpose.

FIGS. 1 through 11, wherein like parts are designated by like reference numerals throughout, illustrate an example embodiment or embodiments of a system and method for capturing the spectral signatures and three-dimensional volumetric data for one or more objects, and determining various characteristics of the one or more objects, according to the present invention. Although the present invention will be described with reference to the example embodiment or embodiments illustrated in the figures, it should be understood that many alternative forms can embody the present invention. One of skill in the art will additionally appreciate different ways to alter the parameters of the embodiment(s) disclosed, such as the size, shape, or type of elements or materials, in a manner still in keeping with the spirit and scope of the present invention. Furthermore, it should be noted that unless otherwise indicated all references to specific wavelengths herein, expressed in, e.g., nanometers (nm), in the detailed description, figures, and claims, are intended to include the specified example wavelength, plus or minus 10%, as would be readily appreciated by those of skill in the art.

FIG. 1 depicts an illustrative system for implementing the aspects of the present invention. In particular, FIG. 1 depicts a system 100 including an object assessment system 102. In accordance with an example embodiment, the object assessment system 102 can be a web connected or cloud connected computing infrastructure that provides a tool for capturing image data for one or more objects, transforming the image data, identifying the one or more objects in the transformed image data, and providing additional characteristics about the one or more objects. As would be appreciated by one skilled in the art, the image data can include any information that can be obtained and/or derived from a captured digital image (e.g., a two-dimensional image or three-dimensional image). For example, the object assessment system 102 can include a cloud based application designed to identify one or more food items, determine a volume for the food items, and determine nutritional values for the food items based on the identification and volume of the food items. Additionally, the object assessment system 102 can evaluate the nutritional intake of a user using before and after meal image data of the food items.

The object assessment system 102 can include a computing device 104 having a processor 106, a memory 108, an input output interface 110, input and output devices 112 and a storage system 114. As would be appreciated by one skilled in the art, the computing device 104 can include a single computing device, a collection of computing devices in a network computing system, a cloud computing infrastructure, or a combination thereof, as would be appreciated by those of skill in the art. Similarly, as would be appreciated by one of skill in the art, the storage system 114 can include any combination of computing devices configured to store and organize a collection of data. For example, storage system 114 can be a local storage device on the computing device 104, a remote database facility, or a cloud computing storage environment. The storage system 114 can also include a database management system utilizing a given database model configured to interact with a user for analyzing the database data.

Continuing with FIG. 1, the object assessment system 102 can include a combination of core modules configured to carry out the various functions of the present invention. In accordance with an example embodiment of the present invention, the object assessment system 102 can include at least an image processing module 116 and an artificial intelligence module 118. The image processing module 116 and the artificial intelligence module 118 can be any combination of software and hardware configured to carryout aspects of the present invention. For example, the image processing module 116 can be configured to capture and perform operations on image data and the artificial intelligence module 118 can be configured to analyze the resulting image data received from the image processing module 116.

In accordance with an example embodiment of the present invention, the input and output devices 112 can include or otherwise be in communication with imaging sensor(s) 120 and lighting source device(s) 122. The imaging sensor(s) 120 and lighting source device(s) 122 can include any combination of sensors or devices capable of capturing images and image data and providing illumination for capturing those images. For example, the imaging sensor(s) 120 can include a single sensor capable of capturing visible, infrared, short wave infrared and near infrared two-dimensional and/or three-dimensional image data of an object. In accordance with an example embodiment of the present invention, the imaging sensor(s) 120 can include any combination of a digital red, green, blue (RGB) camera sensor, a near infrared sensor (NIR), a three-dimensional scanner, or the like, configured to capture and analyze visual image data, spectral signature image data, and three dimensional image data for an object. For example, the imaging sensor(s) 120 can capture image data defined by the characteristics of absorption or emission by wavelength of light incident on the surface of an object. Similarly, the lighting source device(s) 122 can include any combination of lighting sources capable of generating illumination for the imaging sensor(s) 120 to capture the visible, non-visible, and near infrared two-dimensional and/or three-dimensional image data of an object. For example, the lighting source device(s) 122 can include an array of light emitting diodes (LEDs) capable of generating the proper illumination for capturing visual image data, spectral signature image data, and three-dimensional image data by the imaging sensor(s) 120. In accordance with an example embodiment of the present invention, the imaging sensor(s) 120 and lighting source device(s) 122 can be separate devices attached or in communication with the rest of the object assessment system 102. For example, the imaging sensor(s) 120 and lighting source device(s) 122 can be included within the computing device 104 or a separate input and output device 112 in communication through the I/O interface 110 of the computing device 104.

In accordance with an example embodiment of the present invention, the object assessment system 102 can be configured to communicate with other computing devices 124 or components of the system 100 (e.g., the storage system 114, the imaging sensor(s) 120, etc.) over a wireless network, such as a telecommunication network(s) 126. The other computing devices 124 can be implemented as part of the object assessment system 102 and can be tasked to perform any combination of data acquisition, computation, transformation, analysis, and data output. In accordance with an example embodiment of the present invention, the object assessment system 102 can be integrally embedded within the other computing devices 124 and work in tandem with the other computing devices 124 to carry out aspects of the invention. As would be appreciated by one skilled in the art, the other computing devices 124 can include any combination of computing devices, as described with respect to the object assessment system 102 computing device. For example, the other computing devices 124 can include personal computers, laptops, tablets, smartphones, etc. In accordance with an example embodiment of the present invention, the other computing devices 124 can be configured to establish a connection and communicate over telecommunication network(s) 126 to carry out aspects of the present invention. As would be appreciated by one skilled in the art, the telecommunication network(s) 126 can include any combination of wireless networks. For example, the telecommunication network(s) 126 may be combination of a mobile network, WAN, LAN, Bluetooth®, or other type of wireless network technology. The telecommunication network(s) 126 can be used to exchange data between computing devices, exchange data with the storage system 114, and/or to collect data from additional data sources.

Figure 2:
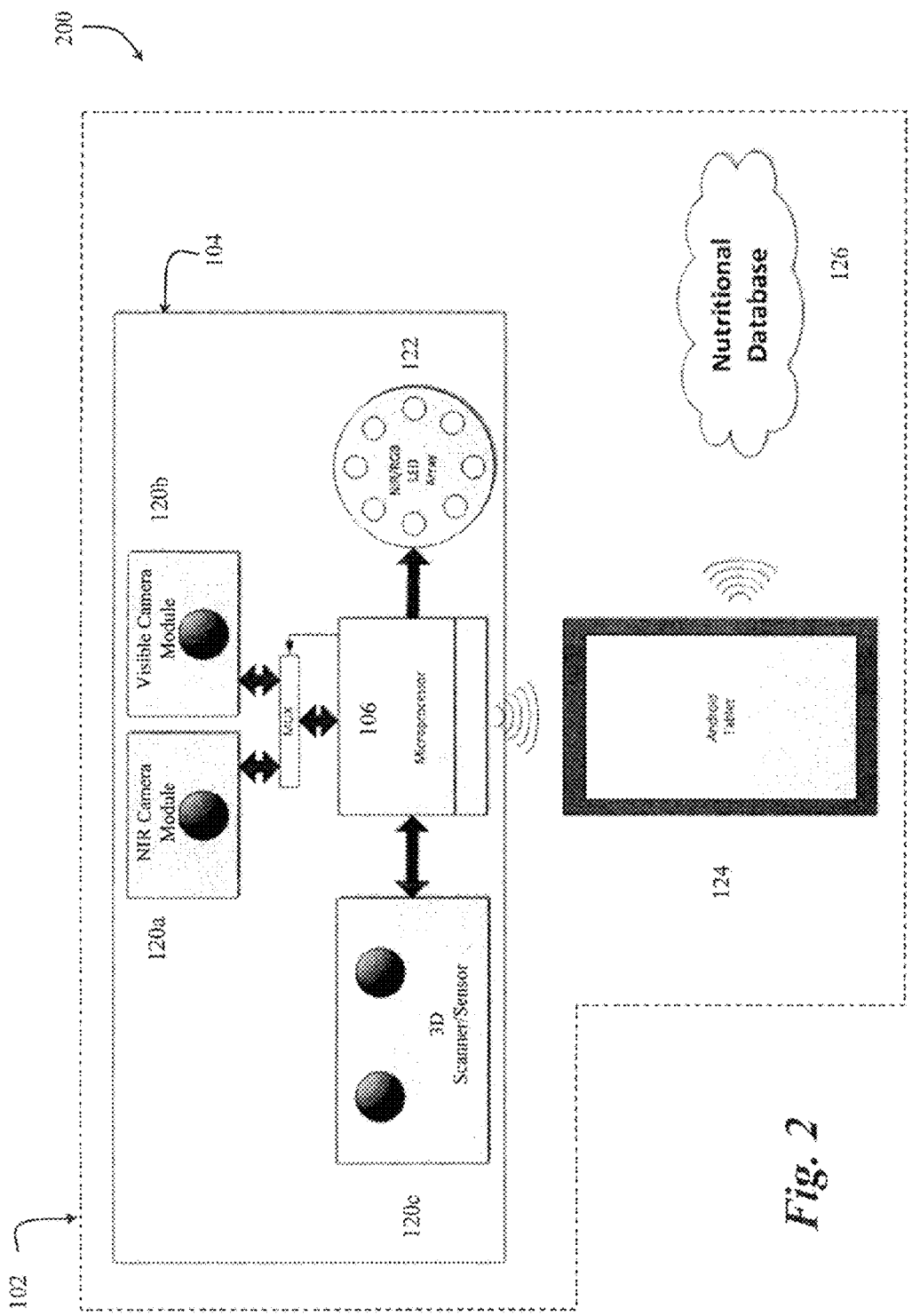
FIG. 2 depicts the system for capturing and automatically determining characteristics of one or more objects, implemented for food item objects, in accordance with aspects of the present invention.

FIG. 2 depicts an illustrative architecture for carrying out an exemplary implementation utilizing aspects of the present invention. In particular, FIG. 2 depicts an exemplary system 200 implementing the object assessment system 102 as discussed with respect to FIG. 1. The system 200, with the object assessment system 102, is configured to capture two-dimensional and/or three-dimensional image data of one or more objects, analyze the captured image data, identify the one or more objects, determine dimensions of the one or more objects, and obtain additional characteristics about the one or more objects. For example, the system 200 can be used to analyze a meal to identify the individual food items in the meal, determine dimensions of the food items (e.g., surface area, volume, etc.), and calculate nutritive values and chemical compositions of meal based on the identified food items and their respective dimensions. The object assessment system 102 as depicted in FIG. 2 includes a computing device 104 housing the components required to carry out the functions of the present invention. In accordance with an example embodiment of the present invention, the computing device 104 includes microprocessor 106 to process at least the capturing of the image data. As would be appreciated by one skilled in the art, the microprocessor 106 can perform a portion or all of the capturing, calculating, determining, analyzing, transforming, etc. steps in accordance with the present invention. The computing device 104 further includes a plurality of imaging sensor(s) 120 communicatively attached to the computing device 104. The plurality of imaging sensor(s) 120 can include a near infrared (NIR) camera module 120a, a visible camera module 120b (e.g., RGB camera module), and a three-dimensional scanner 120c.

The NIR camera module 120a can be any sensor capable of capturing spectral signature image data in the near infrared region of the electromagnetic spectrum. For example, the NIR camera module 120a can be a digital NIR camera sensor with a visible light blocking filter (e.g., with a cutoff of 700 nm+) capable of capturing spectral signature image data in the electromagnetic wavelength spectrum of about 700 nm to 1050 nm. An example of a digital NIR camera sensor is an Omnivision 5647 sensor fitted with a visible blocking filter, such as a Wratten 88A (or similar filter that cuts at 700 nm). Similarly, the visible camera module 120b can be any sensor capable of capturing visible image data in the visible wavelength spectrum region (400 nm to 700 nm). For example, the visible camera module 120b can be a digital RGB camera capable of capturing image data in the spectrum of about 400 nm to 750 nm. An example of a digital RGB camera sensor is an Omnivision 5647 sensor with a NIR blocking filter and a fixed focus module. As would be appreciated by one skilled in the art, there are many combinations of wavelengths that can be included and the ones presented are as examples only. Additionally, the visible camera module 120b can also capture shape and texture data for an object. As would be appreciated by one skilled in the art, the NIR camera module 120a and the visible camera module 120b are capable of capturing an RGB image at different spectral wavelengths. The three-dimensional scanner In accordance with an example embodiment of the present invention, the three-dimensional scanner 120c can be any sensor device capable of capturing three-dimension image data or modeling of an object. For example, the three-dimensional scanner 120c can include a laser, a laser diode, and a sense, a three-dimensional microprocessor configured to capture and analyze the three-dimensional image data. In accordance with an example embodiment of the present invention, the three-dimensional scanner 120c can capture three-dimensional image data without requiring a reference/fiduciary object. As would be appreciated by one skilled in the art, three-dimensional data can be captured using any of combination of stereovision, time of flight, structured light methodologies, or any methodologies known in the art. For example, three-dimensional microprocessor of the three-dimensional scanner 120c can analyze a distance or range from the three-dimensional image scanner 120c to the object (e.g., using time of flight) for a captured image and use the captured image data and the analysis of the range to create a point cloud data output (e.g., in a .txt or .asc file). The three-dimensional image data can include data pertaining to a shape and volume of an object. As would be appreciated by one skilled in the art, a single sensor device can be utilized to perform all the functionality as discussed with respect to camera module(s) 120a, 120b, 120c.

In accordance with an example embodiment of the present invention, the computing device 104 includes lighting source device(s) 122 to provide the necessary illumination for the imaging sensor(s) 120 to capture the various spectral image data. As would be appreciated by one skilled in the art, the lighting source device(s) 122 can include any illumination device(s) capable of creating the necessary illumination to capture data in both visible and non-visible/NIR spectral regions. In accordance with an example embodiment of the present invention, the lighting source device(s)

122 can be a light emitting diode (LED) array including multiple difference colors to simulate the illumination for various spectra. For example, the LED array can include illuminations for five different near infrared spectral wavelengths in a range from about 700 nm to 1100 nm and white light for visible spectral ranges from about 400 nm to 700 nm. As would be appreciated by one skilled in the art, there are many combinations of wavelengths that can be included and the ones presented are as examples only. Additionally, the LED arrays can have a plus or minus 10% from the center wavelength nanometer range, which can be compensated for as needed by the computing device 104.

In accordance with an example embodiment of the present invention, the computing device 104 can include other components communicatively attached to the microprocessor 106 capable of providing data for additional processing and analysis. For example, the computing device 104 can include a wired and/or wireless communication interface (e.g., WiFi, Bluetooth®, cellular, Universal Serial Bus (USB), etc.), a geolocation interface (e.g., a global positioning system (GPS)), a power supply, a microphone, display, speakers, motion sensing device, etc. The wired and/or wireless communication interface can be used to send information from the computing device 104 to a network based application (e.g., on the object assessment system 102, the storage system 114, the other computing devices 124, etc.). For example, if the object assessment system 102 is implemented as a cloud based application or installed on a local computing device (e.g., laptop, desktop, etc.), the computing device 104 can communicate with the rest of the object assessment system 10 over the wire or wireless interface. Similarly, for example, the computing device 104 can communicate directly with an intermediary computing device (e.g., a smartphone, tablet, desktop, laptop computer, etc.) through the wired wireless communication interface and the intermediary computing device can pass the data to the remote object assessment system 102.

In accordance with an example embodiment of the present invention, the geolocation interface can be used to obtain location information of the computing device 104 to be provided to the object assessment system 102. In accordance with an example embodiment of the present invention, the geolocation information can be obtained by a GPS and used by the object assessment system 102 to gather additional information about a particular object. For example, geolocation information can be used to obtain regional menus for a particular restaurant chain when determining nutritional facts about an identified food item. As would be appreciated by one skilled in the art, the computing device 104 can be communicatively attached to or embedded within another device and utilize the wireless interface, microprocessor, and/or geolocation interface of the attached host device. For example, the computing device 104 can be a mobile computing device case plugged into a mobile computing device (e.g., smartphone) and the computing device 104 can utilize the hardware and software of the mobile computing device to perform wireless communications, processing, geolocation, audio visual presentations, etc. In accordance with an example embodiment of the present invention, the system 200 can also include the other computing device 124 and databases 126 (e.g., storage system 114), as discussed with respect to FIG. 1.

FIGS. 3a-3d depict various views of a housing implementations 300 for housing the computing device 104, as discussed with respect to FIGS. 1 and 2. In particular, FIGS. 3a-3d depict the housing implementations 300 that encloses the other components (e.g., imaging sensor(s) 120a, 120b, lighting source device(s) 122, the a wired and/or wireless communication interface, the geolocation interface, a power supply, a microphone, display, speakers, motion sensing device, etc.) of the computing device 104. In accordance with an example embodiment of the present invention, the housing implementations 300 can have approximately the same or similar thickness and width as mobile computing devices (e.g., smartphones) in common usage. For example, the housing implementations 300 can be approximately five and three quarters of one inch in height. As would be appreciated by one skilled in the art, the housing implementations 300 can include a single device, a combination of modules, or a single peripheral device to be connected to another computing device.

In accordance with an example embodiment of the present invention, the housing implementations 300 can include a mounting system. The mounting system can enable the computing device 104 to be attached to a surface, an underside, or encase another object, the location of which is convenient for the user to utilize the object assessment system 102 and the computing device 104. The mounting system can include a mobile computing device case and/or a cabinet bracket. For example, the cabinet bracket enables the device to be attached to an underside of a kitchen cabinet so that information pertaining to food prepared in a kitchen may be conveniently captured and analyzed. In accordance with an example embodiment of the present invention, the computing device 104 can be integrated directly with a mobile computing device in common usage. For example, the housing implementation 300, encasing the computing device 104, can act as the mobile computing device case for the mobile computing device and can be communicatively attached to another mobile computing device 124 (e.g., wirelessly or through an input/output port of the mobile computing device).

Figure 3C:
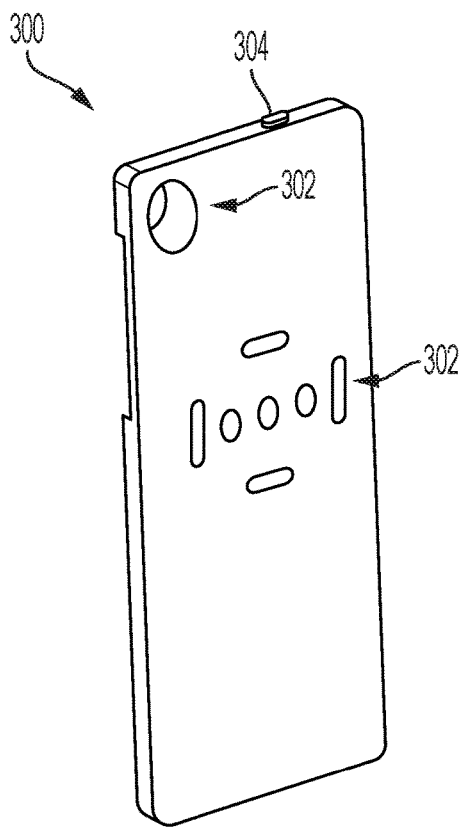
Figure 3C:
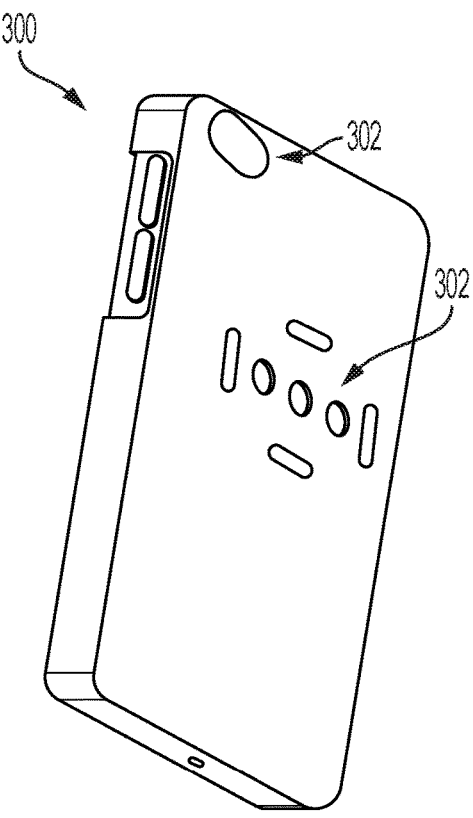
Figure 3C:
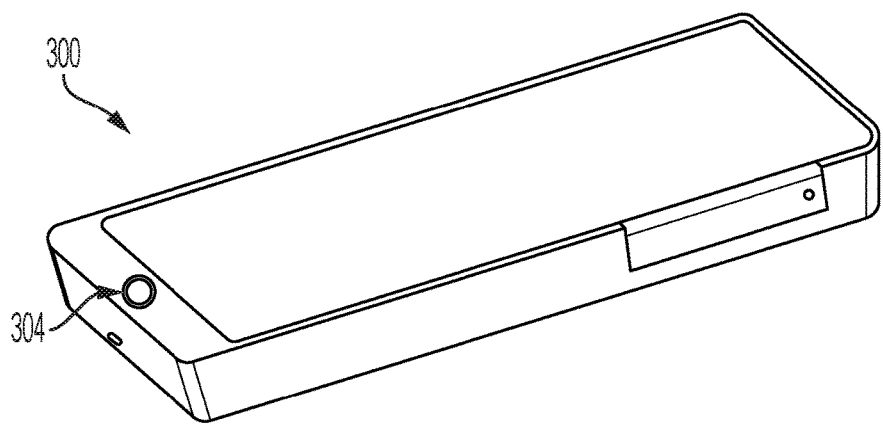
Figure 3D:
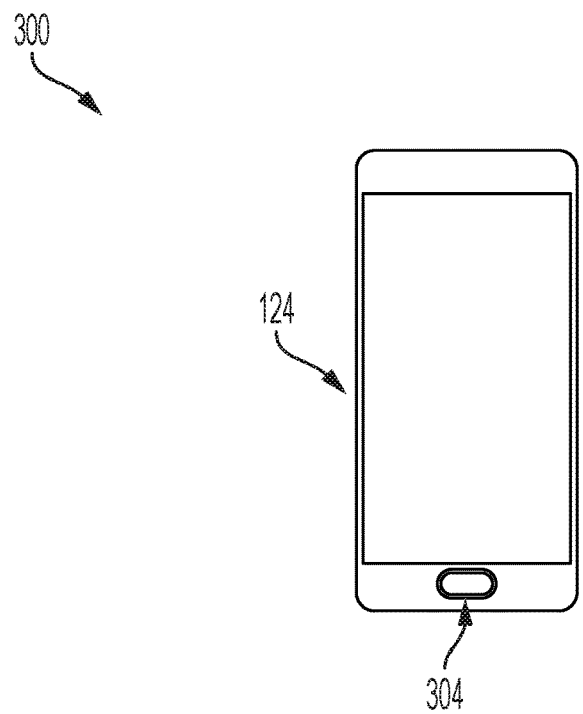
Figure 3D:
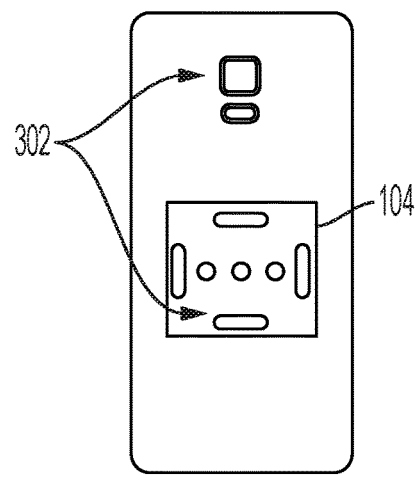

In accordance with an example embodiment of the present invention, the computing device 104 can be integrally embedded within another pre-existing computing device (e.g., the other computing devices 124). FIG. 3d depicts an exemplary representation of the computing device 104 embedding within another computing device. In particular, FIG. 3d depicts the computing device 104 embedding within a smartphone device. Accordingly, the housing implementation 300 is the other computing device 124 and the computing device 104 is integrated within and communicatively attached to the housing implementation 300 (e.g., other computing device 124).

In accordance with an example embodiment of the present invention, the computing device 104 can be used to enable a mobile computing device (e.g., another mobile computing device 124) to operate within the object assessment system 102. In particular, the housing implementations 300 can include the imaging sensor(s) 120a, 120b, lighting source device(s) 122, the a wired and/or wireless communication interface, the geolocation interface, a power supply, a microphone, display, speakers, motion sensing device for use by another mobile computing device 124. The wired communication interface can include a pass through USB, a plurality of adaptors, and a cap. The pass-through USB further can include a pair of female USB inputs. The adaptors can include any combination of male and female USB plugs and can be used to allow the computing device 104 to communicate with other computing devices 124. For example, the USB plugs can be used to connect the I/O interface 110 to another mobile computing device 124 such as a smartphone or tablet over a wired connection. The cap can be inserted into the USB input of the device when the wired connection is not in use. In accordance with an example embodiment of the present invention, the housing implementation 300 can include a plurality of external lenses or windows 302 for the various image-capturing components (e.g., imaging sensor(s) 120 and lighting source device(s) 122).

Continuing with FIGS. 3*a*-3*d*, the housing implementation 300 can include an actuation mechanism 304. The actuation mechanism 304 can include one or more buttons to enable a user to trigger the various components of the computing device 104 by activating the actuation mechanism 304 when the device is in the proximity of one or more target objects. One of skill in the art will appreciate that the exact location and mechanism of the actuation mechanism 304 on the housing implementation 300 can vary and is not limited to that which is shown in the figures. In accordance with an example embodiment of the present invention, the actuation mechanism 304 can be associated with the motion detection sensor, such that when a user waves the computing device 104 over the one or more target objects, the functions of the computing device 104 are activated. For example, the user can "wave" the computing device 104 over a dish containing the food items which will be consumed and the actuation mechanism 304 can be triggered by the motion detection sensor and initiate the imaging sensor(s) 120 and subsequent processing steps as discussed in greater detail herein. In accordance with an example embodiment of the present invention, the housing implementation 300 can include a power supply. The power supply provides electrical current to the various components of the computing device 104 of the present invention. The power supply can include a battery which is rechargeable through the wired connection, a wired power source via a USB input, or any power source known in the art.

In operation, the object assessment system 102, as discussed with respect to systems 100 and 200 depicted in FIGS. 1 and 2, can be used to automatically capture two-dimensional and three-dimensional image data (e.g., visual image data, spectral signature image data, and three-dimensional data) of one or more objects and transform the image data into a format for identification of the one or more objects and determination of a volume for the one or more objects. Thereafter, the object assessment system 102 can use the identification and volume of the one or more objects to determine other desired characteristics about the one or more objects. In an example implementation, the object assessment system 102 can be used to capture two-dimensional and three-dimensional image data of a meal and use the image data to identify the different food items in the meal, calculate dimensions (e.g., volume, surface area, weight, etc.) for each of the food items, and determine nutritional values for an entire meal by summing nutritional values for each of the food items based on their respective volumes.

In accordance with an example embodiment of the present invention, the overall process of the present invention is initiated by targeting one or more objects using the imaging sensor(s) 120 of the computing device 104 and capturing a combination of visible, near visible NIR, and three-dimensional images at a combination of corresponding illuminations. The one or more objects can be any objects in which the object assessment system 102 is calibrated for identification that a user is interested in obtaining additional information about (e.g., dimensions, characteristics, etc.). For example, the computing device 104 and the object assessment system 102 can be calibrated and used to identify food items within a field of view, determine a volume of each individual food items, and subsequently provide nutritional information about the food items based on the volume. As would be appreciated by one skilled in the art, the calibration can include modifying a combination of hardware and software settings for identifying a particular type of objects. For example, the hardware can include the light source device(s) 122 necessary to produce the proper lighting conditions to capture a desired range of spectral images for the particular type of object using the imaging sensor(s) 120. In accordance with an example embodiment of the present invention, the object assessment system 102 can be calibrated to capture specific attributes of one or more objects. For example, the object assessment system 102 can be calibrated to capture characteristic food elements using specific spectral wavelength of 745 nm as a first baseline, 810 nm as a second baseline, 940 nm for fats, 970 nm for carbohydrates/water, and 1020/1050 nm for protein. As would be appreciated by one skilled in the art, the identified wavelengths are for exemplary purposes only and the object assessment system 102 can be configured to capture any combination and range of spectral wavelengths known in the art, with the specific wavelengths determined based on the object or objects being assessed.

The computing device 104 can use a combination of imaging sensor(s) 120 to capture two-dimensional and/or three-dimensional digital images of one or more objects within a field of view. Image data can be extracted from the digital images for use in accordance with aspects of the present invention. As would be appreciated by one skilled in the art, the image data can include any combination of data that can be obtained and/or derived from the digital images captured by the imaging sensor(s) 120. In accordance with an example embodiment of the present invention, the imaging sensor(s) 120 can obtain image data for the one or more objects covering a variety of different electromagnetic wavelengths. For example, the sensor(s) 120 can be a combination of a NIR camera module 120*a* configured to capture non-visible near infrared spectral wavelength image data (e.g., about 700 nm to 1050 nm) and a visible camera module 120*b* configured to capture visible wavelength image data (e.g., about 400 nm to 650 nm). Additionally, the imaging sensor(s) 120 can be configured to capture three-dimensional image data or a three-dimensional model for each of the one or more objects. For example, the imaging sensor(s) 120 can include a three-dimensional scanner 120*c* that can be used to capture three-dimensional image data or construct a three-dimensional model of the one or more objects. As would be appreciated by one skilled in the art, a single imaging sensor or multiple imaging sensors can be used to obtain the image data as discussed with respect to imaging sensors 120*a*, 120*b*, 120*c*.

In instances in which more than one imaging sensor 120 is used to capture the necessary image data, further processing steps can be taken by the object assessment system 102 (e.g., using the microprocessor 106) for sensor fusion. In accordance with an example embodiment of the present invention, digital images (e.g., image data) from multiple imaging sensor(s) 120 can be combined or transformed to create a single representation of a totality of the image data using any methodology known in the art. For example, the object assessment system 102 can utilize sensor fusion to transform multiple sensor image data inputs into a series of vectors that define the response surfaces for each captured one or more object images as a function of spectral wavelength. Each element of the one or more objects can then be represented by spectral functions as defined by the IR reflective responses and the visible spectral responses for the visible light (e.g., color). As would be appreciated by one skilled in the art, if a single imaging sensor is used to capture all of the imaging data, then the sensor fusion processing steps are not necessary. The sensor fusion can be performed by any combination of the microprocessor 106, the image processing module 116, or other cloud computing system.

In accordance with an example embodiment of the present invention, in operation, the light source device(s) 122 can be configured to provide the illumination necessary for the respective imaging sensor(s) 120 to capture the two-dimensional and three-dimensional image data at the desired spectral wavelength ranges. The lighting source device(s) 122 can be any lighting source known in the art that can provide illumination for capturing images at various spectral wavelength ranges. For example, the lighting source device(s) 122 can include an array of light emitting diodes (LEDs) capable of producing illumination for capturing images at visible and non-visible near infrared light spectrum wavelengths. The lighting source device(s) 122 can produce a white light source for capturing the visible light spectrum image data (e.g., RGB) and can use a series of different non-overlapping illuminations for the non-visible near infrared light spectral image data. As would be appreciated by one skilled in the art, lighting source device(s) 122 can produce the necessary illumination by generated lighting from separate red, green and blue LEDs in place of or in combination with the white light source LEDs.

In accordance with an example embodiment of the present invention, an LED array can be used to generate the illumination conditions by cycling through specific wavelength LEDs, configured to produce each of the non-overlapping target wavelengths, and capturing image data at each non-overlapping wavelength. For example, the LED array can include five LEDs and the imaging sensor(s) 120 can capture image data with each LED turned on while the other four LEDs are turned off. As would be appreciated by one skilled in the art, the LED array or alternate lighting source can include any number of LEDs necessary to create the desired illumination environment for capturing image data for a desired non-overlapping spectral wavelength range(s).

In accordance with an example embodiment of the present invention, the array of LEDs can include five NIR LEDS and three visible, Red, Blue and Green (RGB) LEDs. The eight LED array can be used by uniquely modulating the individual LEDs using a Fourier transform method to collect eight wavelengths (e.g., spectral image data produced by the five NIR LEDs and visible image data produced by the three RGB LEDs) simultaneously. Obtaining the eight wavelengths simultaneously can cut the spectral acquisition down to about one second, while reducing the impact of the ambient lighting. In this example embodiment, the image acquisition can be synchronized (e.g., by the image processing module 116) to the modulation wavelengths to would separate ambient (unmodulated) from the spectral signal (modulated). As would be appreciated by one skilled in the art, any number and combination of LED colors and types can be included in the LED array to produce the illumination necessary to capture the image data in accordance with the present invention.

The resulting captured image data at the various non-overlapping spectral wavelengths can be used by the object assessment system 102 for identifying the one or more objects in the captured image. As would be appreciated by one skilled in the art, wavelengths at the actual moment of captured do not need to be non-overlapping because methods of deconvolution can be used to create images that represent non-overlapping wavelengths. The image data for the non-overlapping wavelengths provide sufficient measurements spanning the NIR wavelength spectrum to uniquely characterize most food items. The use of non-overlapping wavelengths makes it more likely to result in image data that better enables identification of the one or more objects in the captured image. Said differently, two overlapping wavelength spectrums would result in two measurements that are undesirably correlated, meaning that if one measurement is large then the other is likely large as well.

Similarly to the sensor fusion processing steps, further processing steps can be taken to optimize the image data captured when using the non-overlapping illumination wavelengths (e.g., deconvolution). In accordance with an example embodiment of the present invention, the image data captured at the different non-overlapping illumination wavelengths can be optimized by removing ambient light sources using methods known in the art. For example, the imaging sensor(s) 120 can capture image data with all of the LEDs in an LED array turned off to create an ambient baseline image. The ambient baseline image can be used to transform all of the images captured while cycling through each specific spectral wavelength LED into images with image data with ambient light removed (e.g., performing a subtraction operation). For example, the image sensor(s) 120 can capture N images (e.g., N=9) with the first image being visible digital images (e.g., visible image data) and the remaining N images (e.g., 8 remaining images) being NIR digital images with a unique LED illumination for each. The image sensor(s) 120 can capture one more image, the N+1 image, with all LEDs turned off. The image processing module 116 can subtract the extra N+1 image from the first N images (e.g., first 9 images) to remove ambient light.

In accordance with an example embodiment of the present invention, the object assessment system 102 can use the imaging sensor(s) 120 or imaging sensors 120a and 120b in combination with the light source device(s) 122 to capture the image data necessary to identify the one or more objects in the captured image. For example, image processing module 116 of the object assessment system 102 can be used to process the signals captured by the imaging sensor(s) 120 of one or more objects and perform any additional processing (e.g., sensor fusion, deconvolution, etc.). Once the image data from the image sensor(s) 120 is captured, processed, and transformed, the object assessment system 102 can perform additional analysis on the processed and/or transformed image data. In accordance with an example embodiment of the present invention, the artificial intelligence module 118 can use the captured, processed, and transformed image data to perform the additional analysis for identification of the objects. As would be appreciated by one skilled in the art, the artificial intelligence module 118 can be trained to identify any particular category or sub-set category of objects. For example, the artificial intelligence module 118 of the object assessment system 102 can be specifically trained to identify food items.

In accordance with an example embodiment of the present invention, the artificial intelligence module 118 can perform a two part analysis on the captured image data from the image processing module 116 to identify the one or more objects. During the first processing part of the analysis, the artificial intelligence module 118 can run an image analysis on the capture image data. The image analysis can be based on the captured visual image data, and the artificial intelligence module 118 can identify individual objects within a field of view. As would be appreciated by one skilled in the art, the field of view can include an entire area of the captured image or a subset of the entire area of the captured image. In accordance with an example embodiment of the present invention, the image analysis can analyze the visual image data to identify unique size, shape and color of one or more objects within the field of view. Once an object is identified as a unique object, the object assessment system 102 can separate the individual object from the other unique one or more objects for additional analysis in the second processing step. The first analysis step can continue analyzing the captured image data until all the unique objects are identified and separated from the rest of the one or more objects. For example, food items can be identified visually based on an analysis of a unique size, shape, texture, color, etc. The unique size, texture, shape, and color of a food item can provide a unique set of image data that can be analyzed by a computer algorithm(s) based on recognized pattern matching against known unique sizes, textures, shapes and colors in a database (e.g., the storage system 114). For example, brussels sprouts can be identified by pattern matching their unique size, or size range, color (particular shade of green), texture, and/or shape. In accordance with an example embodiment of the present invention, the visual image data can be transformed into a color histogram to be used during smart pattern recognition or pattern matching by the artificial intelligence module 118, as discussed in further detail with respect to FIG. 5.

Figure 4:
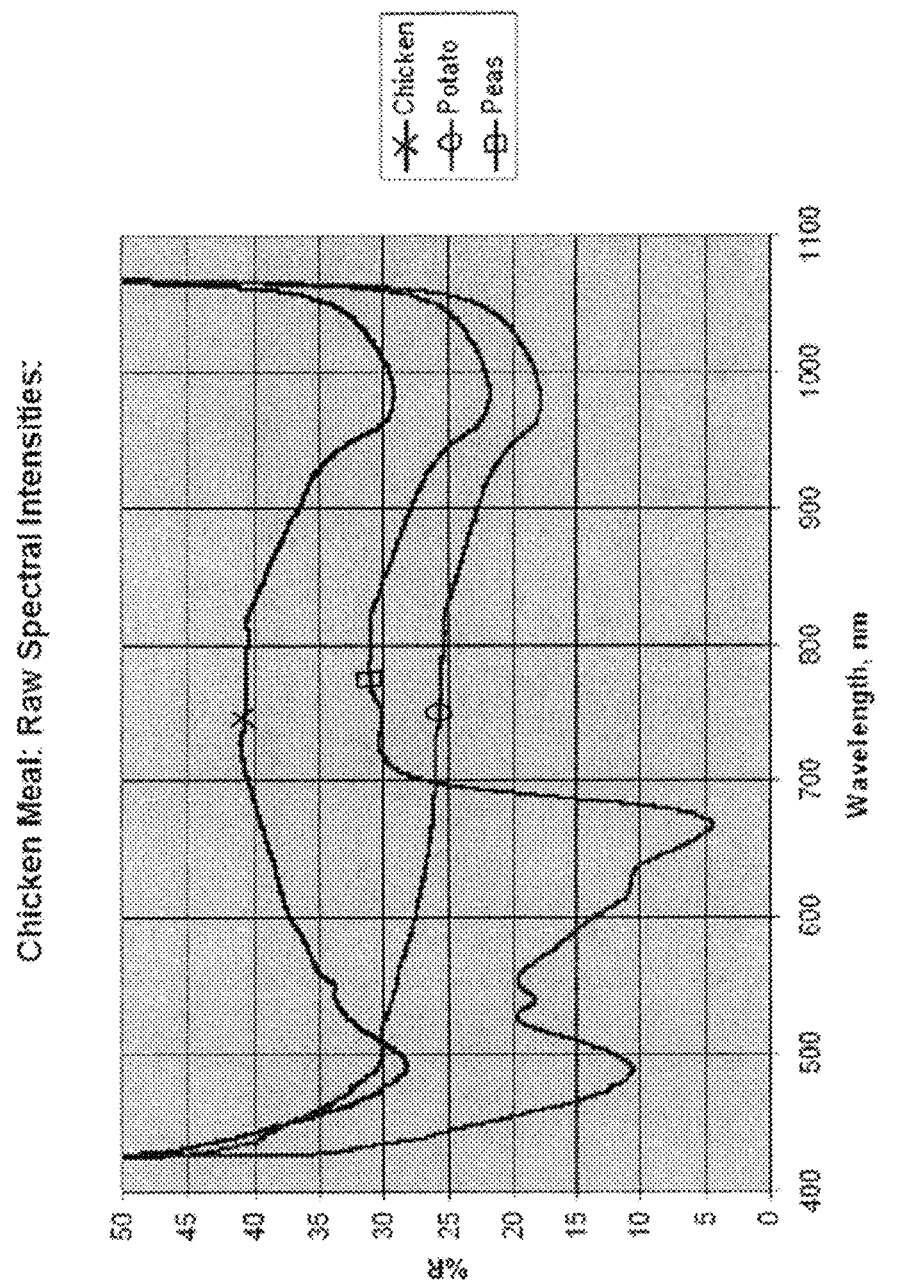
FIG. 4 is a graphical representation of raw spectral data captured, interpreted, and utilized by the system, in accordance with aspects of the present invention.
Figure 5:
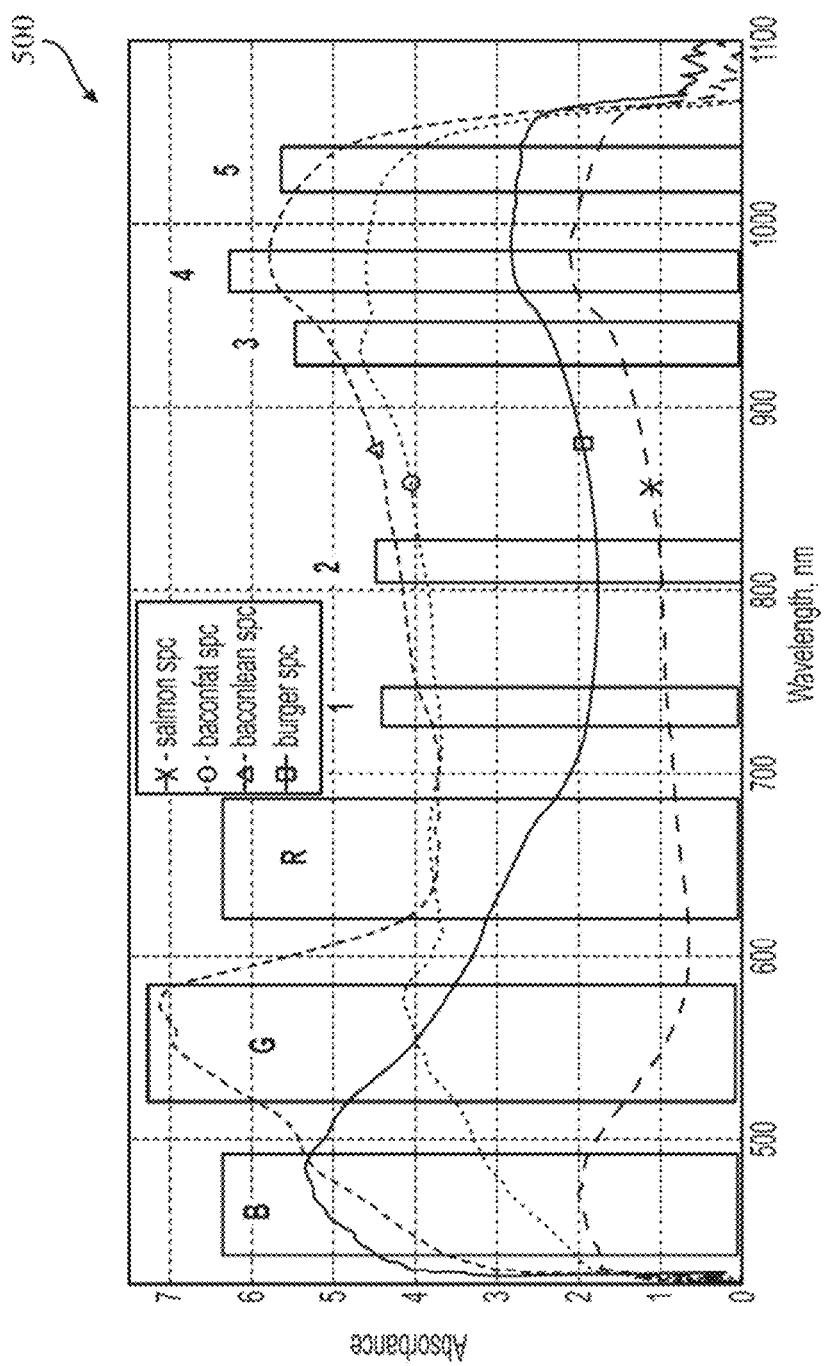
FIG. 5 is a graphical representation of spectral signature data derived from the captured image data and utilized by the system, in accordance with aspects of the present invention.

In accordance with an example embodiment of the present invention, the image processing module 116 and/or the artificial intelligence module 118 can create a unique spectral signature for each of the separated objects from the first processing part. In particular, the image processing module 116 and/or the artificial intelligence module 118 can use the spectral image data obtained from the imaging sensor(s) 120, at the various spectral wavelength ranges, to transform captured image data to create the unique spectral signature for each of the separated objects. An example of the various spectral ranges captured from the raw spectral response (spectral image data) is depicted in FIG. 4. In particular, FIG. 4 shows the true spectral reflectance of multiple food items (e.g., chicken, potato, and peas). In accordance with an example embodiment of the present invention, the spectral image data, as depicted in FIG. 4, can be used to create a spectral signature for each of the one or more objects in a captured image. For example, the image data can be transformed into a spectral signature (e.g., utilizing combined visible, RGB, and NIR image data) as represented in the graph in FIG. 5. In particular, FIG. 5 depicts a graphical representation of raw image data, in histogram form, captured by the imaging sensor(s) 120 when targeting a meal includes chicken, potato, and peas as food items within the meal. The image data for each food item transformed and plotted as an implied absorption or log 1/R (R=reflectance) response against the wavelength in nanometers. As shown in FIG. 5, each plotted food item (e.g., salmon, bacon fat, bacon lean, and burger) has a unique response pattern (e.g., spectral signature) which can be attributed to that food item and used for identification. As would be appreciated by one skilled in the art, the graphs depicted in FIGS. 4 and 5 are merely for illustrative purposes and the graphical data would be organized and stored in a different format.

In accordance with an example embodiment of the present invention, the second processing portion of the analysis can utilize spectral analysis to further identify objects and/or properties of the objects. In particular, the artificial intelligence module 118 can be trained to perform a spectral analysis on the individually segregated objects and their respective spectral signatures. The spectral analysis can include performing a cross correlation of the spectral image data of the objects with previously recorded known spectral wavelengths stored in a database. As would be appreciated by one skilled in the art, the previously recorded known spectral wavelengths stored in the database can be resulting spectral wavelengths created from samples of all of the objects that the object assessment system 102 is programmed to identify. The artificial intelligence module 118 is trained to perform pattern matching between using the known spectral signatures in the database with the spectral signatures created from the capture image data. The pattern matching of the artificial intelligence module 118 can include any known combination of algorithms for accurately predicting a matching pattern. For example, the artificial intelligence module 118 can scan through the spectral signatures in the data base to find the closest matching spectral signature, and determine that the closest matching spectral signature is the identity of the object. As would be appreciated by on skilled in the art, the artificial intelligence module 118 can identify one or more objects and/or characteristics of those objects based on a predetermined threshold within the pattern matching.

In accordance with an example embodiment of the present invention, the artificial intelligence module 118 can be trained for identification of the one or more objects. The logic of the artificial intelligence module 118 can be based on machine learning and training the artificial intelligence to recognize objects based on a combination of visible and near infrared image data. The artificial intelligence module 118 can be trained to associate a unique size, shape, and texture of the one or more food items in addition to the particular spectral signature (e.g., color). Similarly, the artificial intelligence module 118 can be trained to associate a particular spectral signature with a particular object, the association can be stored in a database (e.g., the storage system 114). Prior to training the artificial intelligence module 118, a knowledge database must be constructed for one or more objects to be identified in the future by the object assessment system 102. For example, a user who is programming the object assessment system 102 can scan in all of the food items that are desirable to identify and spectral signatures are created for each of the food items. As would be appreciated by one skilled in the art, the database can constantly be updated with new object entries created by a combination of the service provider and the user base. These recordings, for all of the food items, along with the name of the food items are given to an AI training module which trains the AI.

In accordance with an example embodiment of the present invention, an image sample of an object can be acquired, using the object assessment system 102 or an alternate training system, using a neutral background. Information about the acquired object can be manually entered into the system and will be associated with the object in the database for use by the artificial intelligence module 118. For example, the name and actual weight of the object can be recorded within a TIFF and/or CSV file. Additionally, a region of interest can be selected within the acquired image of the object (limited to the boundaries of the object). A plurality of image planes (e.g., twenty one planes) for the selected region of interest for the object can be obtained and stored in the TIFF file. Each unique object will have a separate file (e.g., separate CSV file) to be used to train the artificial intelligence module 118. Once a library of files (e.g., CSV files) has been created, the artificial intelligence module 118 can begin the training process. As would be appreciated by one skilled in the art, the knowledge database can be constructed using any methodology and systems known in the art and the artificial intelligence module 118 can be trained using any of those methodologies and systems.

Figure 6:
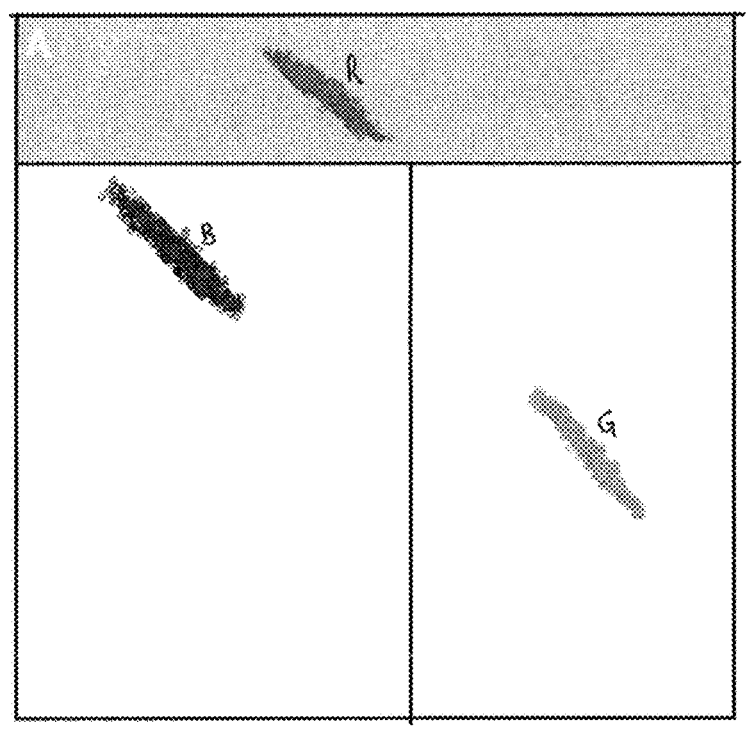
FIG. 6 is a cloud plot including numerous pixel data points obtained using the system, in accordance with aspects of the present invention.

In accordance with an example embodiment of the present invention, the spectral signatures transformed from the image data, to be used by the artificial intelligence module 118, can be represented as a vector of scalar values. The vector of scalar values can be used in pixel classification during identification of one or more objects by the artificial intelligence module 118. For example, the visible light image data can include three colors (e.g., red, green, blue) and the near infrared image data can include fifteen colors (e.g., three colors for each image captured at five particular non-overlapping wavelengths) and combine to form a vector of eighteen colors for each pixel. Similarly, in accordance with another example embodiment, the image data from the five particular non-overlapping wavelengths can be averaged to create a single monochrome pixel value for a vector of eight colors for each pixel. Continuing the example, taking the vector of eighteen color values, the vector can be represented by an eighteen dimensional hypercube (e.g., camera pixels range from 0.0 to 1.0 to create possible combinations in 18 dimensions). Because the pixels of a particular object should be relatively consistent, then all the points from the pixels of that object will land within a close proximity of one another in the eighteen dimensional cube. Thought of otherwise, the pixel classification can be thought of as plotting a large collection of data points derived from the image data to create a cloud of data points. For example, a blue object can have a cloud of blue data points clustered together within an identifiable boundary, such that the artificial intelligence module 118 can identify an occurrence of the particular blue object in a captured image when it falls within the pre-identified set of boundaries corresponding to that particular object. FIG. 6 depicts an example of particular clouds including numerous pixel data points. The particular clouds can be divided in multiple segments based on color (e.g., spectral regions) and boundaries can be established for landing regions associated with those colors. For example, as depicted in FIG. 6, the particular clouds can be divided into three clouds and boundaries representing each of the red, blue, and green color regions (RGB) such that if the pixels of the objects land into the top boundary region, then it can be determined that an object is a red object. As would be appreciated by one skilled in the art, the artificial intelligence module 118 can use any combination of algorithms to determine the boundaries for classifying particular objects. For example, the artificial intelligence module 118 can use a K-nearest neighbors technique, a support vector machine, a decision tree, a Bayesian estimation, a neural network, other methodology known in the art.

Once the database has been populated with a sufficient collection of spectral signatures, the artificial intelligence module 118 can make inferences about image data captured by the imaging sensor(s) 120 and make an identification of the one or more objects within the captured image data. For example, the artificial intelligence module 118 can compare data points (e.g., the pixel hypercubes, boundaries, etc.) from the received image data and compare the data points to data points for the existing known spectral signatures in the database. From the comparison the artificial intelligence module 118 is able to make a determination whether the one or more objects from the captured image (e.g., the image originating the image data) sufficiently matches a known object.

In accordance with an example embodiment of the present invention, the artificial intelligence module 118 can be trained to identify a unique chemical composition of an object by identifying a unique pattern associated with that object using a weighted matching metric. For example, proteins (e.g., about 1050 nm) have a different spectral wavelength reflection than carbohydrates (e.g., about 970 nm). As would be appreciated by one skilled in the art, the spectral wavelengths can be selected based on signature components of a material in terms of a chemical composition (e.g., from standard responses for known chemical substance). In accordance with an example embodiment of the present invention, the second level of identification/matching utilizes a chemical characterization based on classical food components, such as fats, carbohydrates, proteins to define the macro nutrients, and spectral color imaging to help classify the food group in terms of meats, vegetables, etc. these latter components are linked more to a lookup matching rather than an absolute component type determination. For example, the artificial intelligence module 118 interprets the spectral image data from an isolated sample food element by segmenting the data into, e.g., eight separate channels that represent functional elements of the food. For example, hemoglobin containing (red meat), chlorophyll containing (green vegetables), fat containing (NIR 940 nm), carbohydrate/water containing (NIR 970 nm) and protein containing (NIR 1020 nm . . . detected by 1050 nm LED). This spectral analysis of the food materials is derived from a combination of visible image data (extracted from a computed color histogram as depicted in FIG. 5) and near infrared image data composition based analysis obtained from the reflected image from specific wavelength light sources (e. g., using NIR). For example, the combined visual image data and spectral image data can be transformed into spectral correlations for an object as represented in the graph in FIG. 5. FIG. 5, in an example embodiment, depicts a graphical representation of the visual image data and the spectral image data captured by the imaging sensor(s) 120 when targeting a meal including salmon, bacon fat, bacon lean, and burger as food items within the meal. The image data for each food item transformed and plotted by implied absorption or log 1/R response against the wavelength in nanometers. As shown in FIG. 5 each plotted food item has a unique pattern (e.g., spectral correlation) that can be used by the artificial intelligence module 118 to identify an object.

In accordance with an example embodiment of the present invention, additional data can be collected by the object assessment system 102 and/or stored in the database to be used in any analysis, determination, transformation, and calculating steps. The computing device 104 can include additional components for collect additional data through a bar code scanner, optical character recognition, audio cues, volatile organic compound (VOC) sensor, manual input from a user, etc. For example, the input and output device can use the bar code scanner to read information from a barcode, the character recognition can recognize an ingredients list, the microphone can capture verbal description of a food items spoken by the user, etc. In accordance with an example embodiment of the present invention, the object assessment system 102 can be configured to utilize a spectrometer in combination with the imaging sensor(s) 120. The combination of the imaging sensor(s) 120 and the illumination source device(s) 122 can act comparably to a spectrometer by processing the image data in the same way that spectral data from a spectrometer is processed. As would be appreciated by one skilled in the art, imaging sensor(s) 120 can be utilized for emission spectroscopy, direct absorbance or reflectance spectroscopy, or raman spectroscopy. In accordance with an example embodiment of the present invention, the imaging sensor(s) 120 can include a micro electrical mechanical spectrometry chip set further including an IR source, a plurality of condenser lenses, a slit, an IR band pass filter, a diffraction grating, a digital micromirror device, a detector, and a microprocessor. The imaging sensor(s) 120 can output information pertaining to the spectral signature of items of food, possibly in graphical form plotting absorbance as a function of wavelength or wavenumber (inverse wavelength).

In accordance with an example embodiment of the present invention, the three-dimensional image data received from the imaging sensor(s) 120 can be used by the image processing module 116 to determine the dimensions of the one or more objects (e.g., surface area, volume, weight, density etc.). As would be appreciated by one of skill in the art, determining the dimensions of the one or more objects can be performed independently of the identification steps as discussed herein. The image processing module 116 can use the three-dimensional image data to determine a volume, weight, and density of the one or more objects using functions that are derived by visible imagery and three-dimensional imaging. The volume, weight, and density can be obtained by the image processing module 116 without the aid or need of a fiduciary or reference object for scale. In accordance with an example embodiment of the present invention, the volume can be determined utilizing x, y, z coordinates for one or more objects. In accordance with an example embodiment of the present invention, the z coordinate can be determined by determining a distance or range from the imaging sensor(s) 120 and the targeted object. The distance or range (e.g., the z coordinate) can then be used in calculating the x and y coordinates. In particular, the z vector can be used to calculate a number of pixels in the image for the remaining coordinates (e.g., the x, y vectors). In particular, the imaging sensor(s) 120 can detect the distance of a pixel from the camera using the field of view of the camera as a reference, and can be calibrated to give coordinates x, y and directly measures size and shape of the one or more objects. By counting the pixels and getting the size and shape, the image processing module 116 can calculate a surface for the one or more objects. Using range and surface area of the one or more objects, other dimensions (e.g., weight, volume, etc.) can be calculated by the image processing module. In accordance with an example embodiment of the present invention, the volume and weight for an object can be calculated in relation to the visual image data.

In accordance with an example embodiment of the present invention, the determination of dimensions for each of the one or more objects using the three-dimensional image data can be used to identify the volume of different food items within a plated meal (or other types of objects on other surfaces). As would be appreciated by one skilled in the art, the determination of the x, y, and z coordinates as it relates to a plate of food is an exemplary example and it is not limited to calculating the dimensions of food items. Continuing with the example embodiment, the three-dimensional scanner 102c (or other imaging sensor(s) 120) can be used to capture a depth or range between the three-dimensional scanner 102c and the plate of food items. The image processing module 116 can identify a bottom surface and a top surface. For example, the bottom surface can be identified as the plate or plate outline where the food items are positioned and the top surface can be the three-dimensional surface area/shape of the food item(s) on the plate. If the entire plate outline cannot be determined to identify a shape of the plate, a visible region plate can be used to create the shape of the plate. In particular, the image processing module 116 can identify the pixels of the image that correspond to the plate with no food sitting on the surface to occlude the view of the plate and use the plate pixels to recreate the plate surface. For example, assuming a symmetric plate, the system can project a visible region of the plate at a central point and iterate the shape across 360 degrees to create the overall plate shape. As would be appreciated by one skilled in the art, any object can be used to represent the bottom surface in relation to the one or more objects being identified and the example of the plate is not intended to be limiting. For example, keeping with the food example, a bowl, a countertop, a table top, etc. could be used as a bottom surface when determining volume of the food items.

The determined plate shape (or other object shape) along with the three-dimensional surface area/shape of the food items can then be used to determine the volume of each food item on the plate. With the plate pixels derived from the three-dimensional image data from the three-dimensional scanner 102c, the image processing module 116 can use the three-dimensional image data to determine a three dimensional shape of the plate (e.g., using the x, y, z coordinate) and food items on the surface of the plate. The x, y, z coordinates can be calculated using the identified bottom surface (e.g., the plate) and the top surface (e.g., a surface area of the food items). In particular, a pixel cube can be created from the three-dimensional image data and the dimensions of the pixel cube (e.g., the depth between the bottom surface and the top surface for a z value and the known lateral pixel values based on a distance from the sensor for the x, y, values) can be used to determine a volume measurement for the pixel cube. The volume for the pixel cube can be applied to all of the pixels that correspond to the surface of each food item, and therefore the volume of each food item can be determined by summing all of the correlating pixel volumes. Accordingly, the identification of the bottom surface is used during the volumetric calculation as a representative depth value (e.g., in relation to a top surface of the one or more objects). The bottom surface (e.g., a plate) is not used as a fiduciary object as relied upon in traditional methodologies. In other words, an established bottom surface (e.g., a plate) provides the difference between that bottom surface and an upper surface (z coordinate) to be used with the x and y coordinates to calculate volume of an object without requiring use of a fiduciary object as a reference for scale.

In accordance with an example embodiment of the present invention, the volume data for the food items can be used to determine at least a weight, density, and caloric values for the particular food items. The density can be determined by utilizing identity of the food item, provided by the artificial intelligence module 118, and retrieve from the database the density of that particular food item. From the volume and density, the particular weight for the food items can be calculated. Using the weight, the object assessment system can retrieve the conversion of weight into calories for that particular food item from the database.

Figure 7:
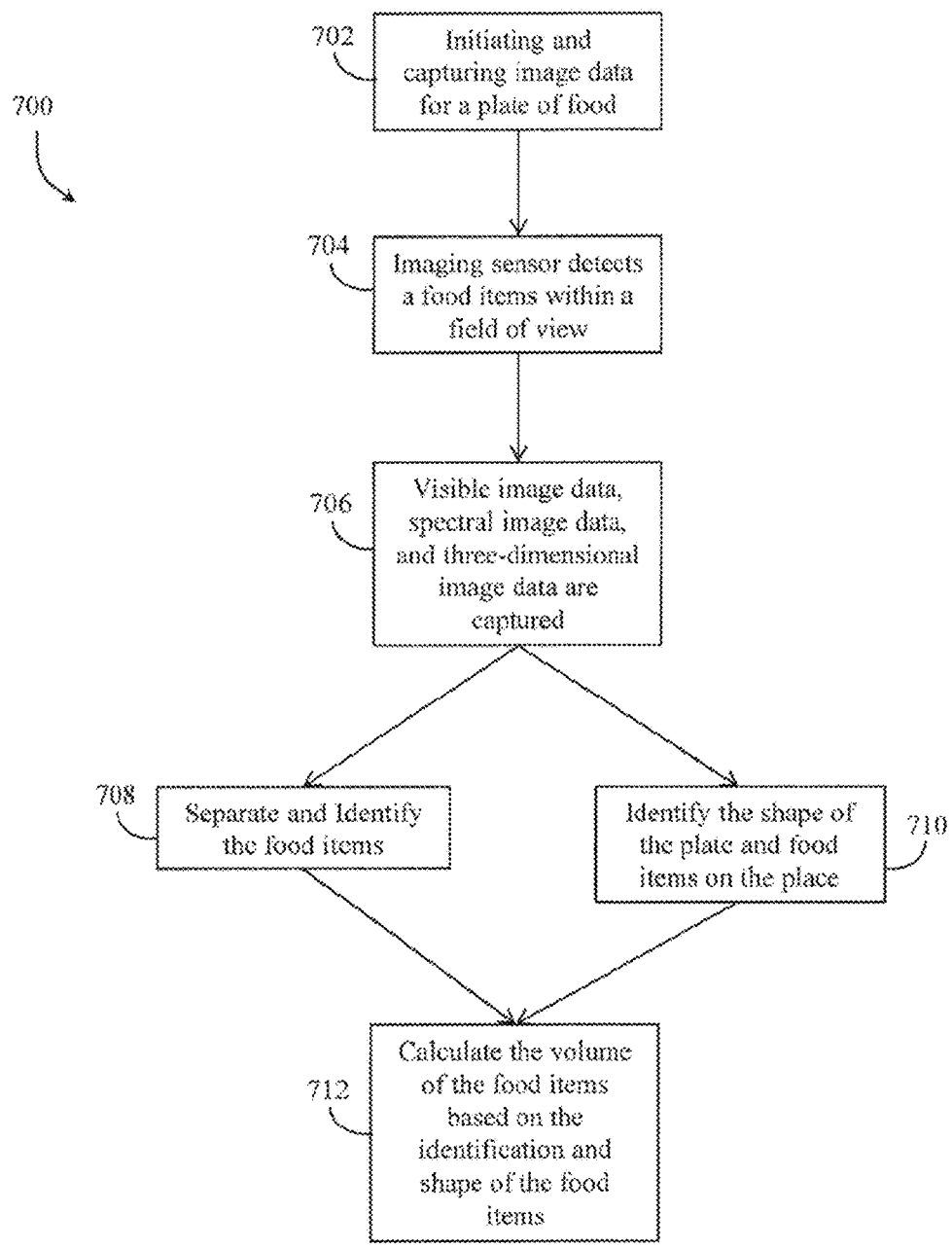
FIG. 7 is an illustrative flowchart depicting an example process utilizing the system for food item assessment, in accordance with aspects of the invention.
Figure 8:
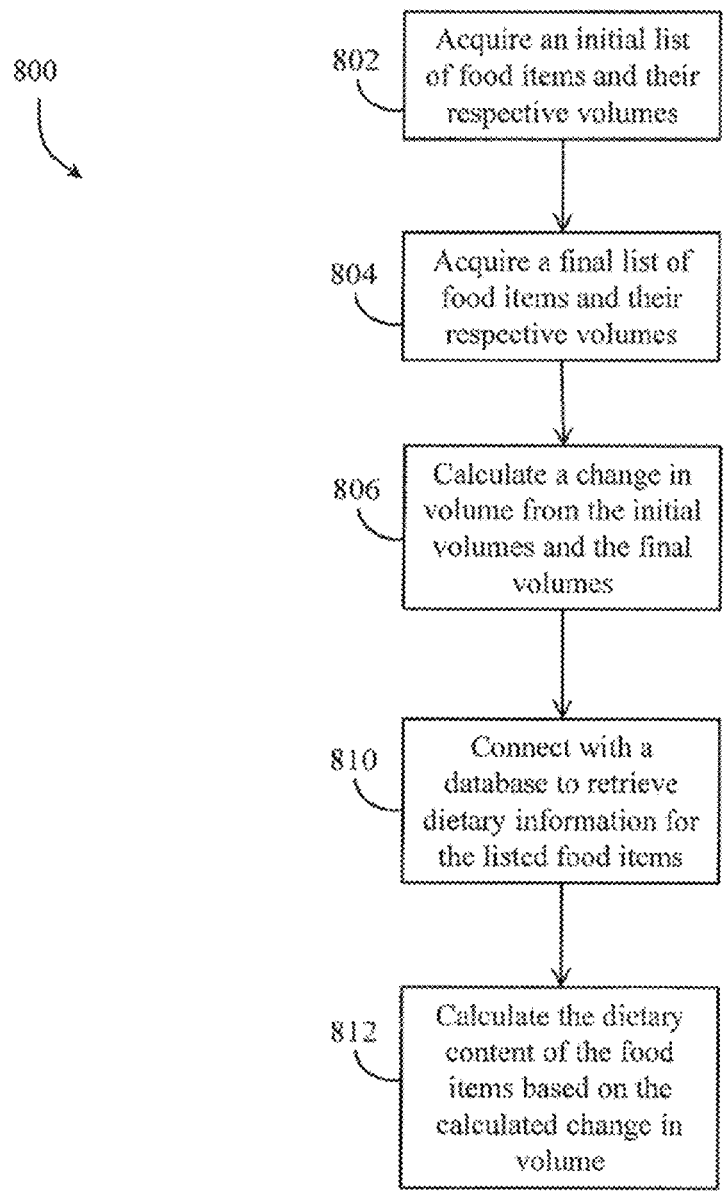
FIG. 8 is an illustrative flowchart depicting an example process utilizing the system for food item assessment, in accordance with aspects of the invention.

FIGS. 7 and 8 show exemplary flow charts depicting implementation of the present invention. Specifically, FIG. 7 depicts an exemplary flow chart showing the operation of the object assessment system 102, as discussed with respect to FIGS. 1-6. In particular, FIG. 7 depicts a process 700 in which the object assessment system 102 captures images of a meal and provide nutritional information about the food items in the meal. At step 702, the process initiates by a user triggering the imaging sensor(s) 102 over a plate of food. For example, the user waves the computing device 104 over the plate of food and initiates the object assessment system 102. The waving of the computing device 104 over a plate of food can trigger a motion sensing actuation mechanism 304 to transmit a signal to activate the imaging sensor(s) 102 to capture the image data. Once the image capturing process has been initiated the user should hold the computing device 104 at a stationary position to clearly and accurately capture the image data. In accordance with an example embodiment of the present invention, the computing device 104 can display an indication that the capturing process has been initiated with instructions to the user to hold the computing device 104 stationary over the target objects until the imaging sensor(s) 102 have completed capturing the image data. As would be appreciated by one skilled in the art, the imaging sensor(s) 102 can be activated by another means (for example, pressing an actuator/button implementation of the actuation mechanism 304).

At step 704, the imaging sensor(s) 102 detects a plate setting on a table and triggers the imaging sensor(s) 102 to capture image data for the plate of food. For example, the imaging sensor(s) 102 uses the three-dimensional image data to detect edges of a plate based on a difference of depth between the plate and a surface of the table at the edges of the plate. As would be appreciated by one skilled in the art, the imaging sensor(s) 102 can identify another object or objects within a field of view and is not limited to identifying a plate. At step 704, the image processing module 116 can also determines a range or distance between the imaging sensor(s) 102 and the plate. In accordance with an example embodiment of the present invention, the image processing module 116 can recognize the plate by identifying predetermined plate primitives from a collection of plate primitives stored in the storage system 114. When the plate is detected, the imaging sensor(s) 102 are instructed to capture image data for the plate. As would be appreciated by one skilled in the art, if multiple plate settings exist, the object assessment system 102 can capture image data for each plate setting or for a single centered plate setting.

At step 706, the imaging sensor(s) 102 captures visible image data, spectral image data, and three-dimensional image data and the image processing module 116 stored the captured image data for additional processing. The visible image data, spectral image data, and three-dimensional image data are automatically obtained for the entire plate of food items, as discussed with respect to FIGS. 1-6. For example, the image sensor(s) 102 can capture visible image data (e.g., using an RGB sensor 102b) in a single image capture and capture spectral image data (e.g., using NIR sensor 102a) by capturing a sequence of images while simultaneously triggering a unique illumination wavelengths (e.g., using LED array 122) for each desired NIR. At step 708, each of the separate images and set of images are processed by the image processing module 116 and the artificial intelligence module 118, as discussed with respect to FIGS. 1-6. For example, the visual image data is used to identify and separate the individual food items based on the unique, size, shape, texture, and color of the food items using pattern matching by the artificial intelligence module 118. Similarly, the spectral image data is used to determine unique spectral signatures for each separate food item by performing cross matching by the artificial intelligence module 118.

At step 710, the image processing module 116 can identify the pixels of the image that correspond to the plate with no food sitting on the surface to occlude the view of the plate. With the plate pixels, the image processing module 116 can use the three-dimensional scanner 102c to determine a three dimensional shape of the plate (e.g., using the x, y, z coordinate). In accordance with an example embodiment of the present invention, if the entire plate outline cannot be determined to identify a shape of the plate, a visible region plate can be used to create the shape of the plate. For example, assuming a symmetric plate, the system can project a visible region of the plate at a central point and spin the shape 360 degrees to create the plate shape. The determined plate shape along with the three-dimensional surface area/shape of the food items can then be used to determine the volume of each food item on the plate. At step 712, using the identification from step 708 and the pixel size determination of step 710, the image processing module 116 can calculate a volume of the food items. For example, the image processing module 116 can count the number of pixels in each identified food item and then use the number of pixels to determine a volume. As a result of the process 700 of FIG. 7, the object assessment system 102 can use the computing device 104 to capture image data for a plate of food, identify the food items on the plate, and determine a volume for each of the food items.

FIG. 8 depicts a process 800 that uses the identification information and volume information of the food items from FIG. 7 (FIGS. 1-6) to determine a nutritional value for the food items. At step 802, the image processing module 116 can acquire an initial list of food items and their respective volumes. For example, the image processing module 116 can obtain the list of food items and their respective volumes from the identified food items, as identified in the steps of FIG. 7. At step 804, the image processing module 116 can acquire a final list of food items and their respective volumes. For example, similarly to step 802, the image processing module 116 can acquire the list of food items and respective volumes from the steps of FIG. 7. At step 806, the image processing module 116 can calculate a change in volume from the initial volumes and the final volumes. For example, the image processing module 116 can calculate the different between the initial volumes of the food items in step 802 and the final volumes of the food items in step 804 using a subtraction operation. At step 808, the image processing module 116 can connect with a database to retrieve dietary information for the listed food items. For example, the image processing module 116 can contact the FDA and/or the United States Department of Agriculture (USDA) databases and request nutritional information for the list of food items from step 802. At step 810, the image processing module 116 can calculate the dietary content of the food items based on the calculated change in volume. For example, the image processing module 116 can use the nutritional information obtained from the FDA and/or the USDA databases and calculate the dietary content of the food items based on the amount of change in volume calculated in step 806.

In accordance with an example embodiment of the present invention, end users can use the object assessment system 102 to perform tasks related to identification of one or more objects, determining a volume of the one or more objects at various points in time, and gather additional information about the one or more objects based on the identification and determination steps. For example, end users can use the object assessment system 102 as part of a dietary tracking application to automatically identify food items and the nutritional information associated with those food items. As would be appreciated by one skilled in the art, the object assessment system 102 can be used to identify and perform additional analysis on any combination of identifiable objects.

Figure 9:
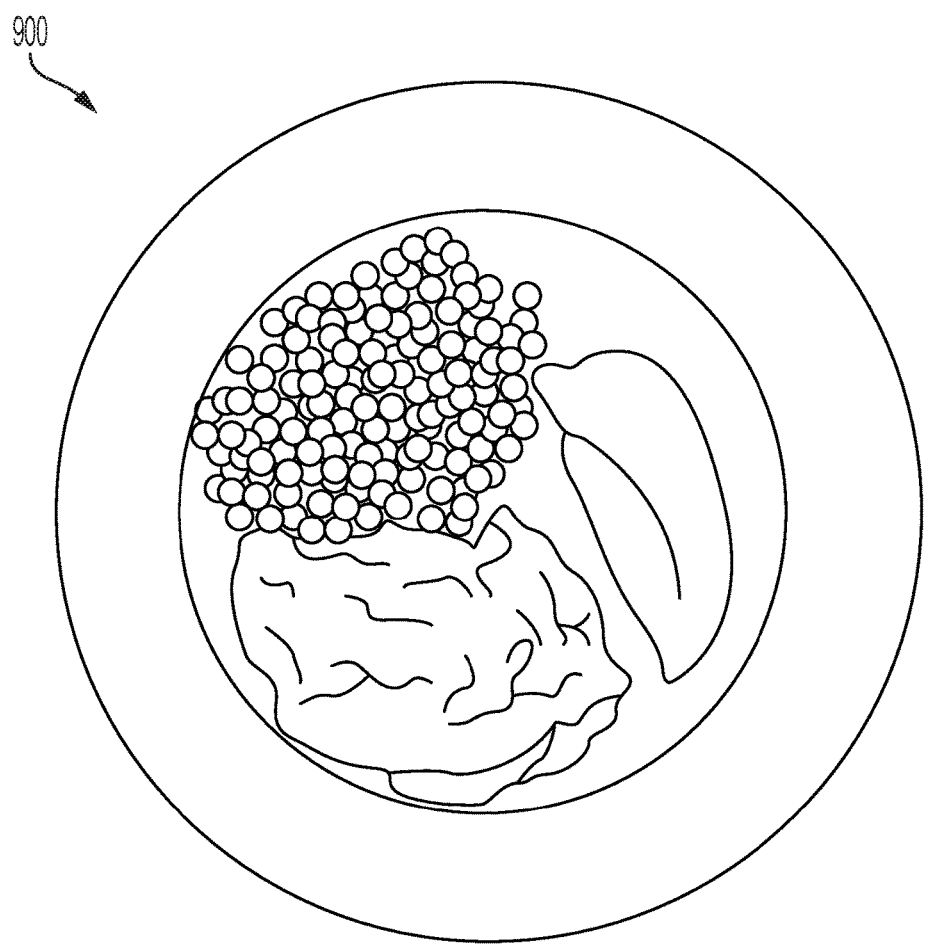
FIG. 9 is a depiction of a meal to be captured and processed, in accordance with aspects of the invention.

The following example is an exemplary example of a particular application of the object assessment system 102 as it applies to the identification of food items. The present invention is not intended to be limited to the identification of food items and the example is merely for illustrative purposes. Following prompts on the dietary tracking application, the end user would use the computing device 104 to capture image data of a meal before any consumption of the meal has taken place. In accordance with an example embodiment, an end user can initiate the object assessment system 102 by triggering an actuation mechanism 304 on the computing device 104. The actuation mechanism 304 can be initiated by "waving" the computing device 104 over the dish containing the meal which will be consumed. An example of a meal can be seen in FIG. 9. In particular, FIG. 9 depicts a meal including three separate food items, peas, chicken, and mashed potatoes. The "waving" initiates an automatic process that begins by automatically instructing the imaging sensor(s) 102 to identify the plate/plate shape, depth to the plate, capture visual image data, spectral image data, and three-dimensional image data of the entire meal. All of the image data is automatically obtained by the image sensor(s) 102 and is passed to the image processing module 116 and the artificial intelligence module 118 for additional processing. As discussed with respect to FIGS. 1-8, the image processing module 116 and the artificial intelligence module 118 can use the captured image data to separate the individual food items (e.g., peas, chicken, mash potatoes), identify the separated food items, calculate a volume of the food times (e.g., using the three-dimensional image data), and determine a nutritional value of the food items in the initial meal. As would be appreciated by one skilled in the art, the nutritional values can be retrieved from a database by looking up the nutritional values for the identified food items and calculating the nutritional values based on the determined volume (portion size) of the food items. In accordance with an example embodiment of the present invention, the object assessment system 102 can contact a remote database (e.g., the FDA and/or the USDA databases) to gather the nutritional value for the food items.

As would be appreciated by one skilled in the art, the end user can add additional information about the meal to be used during analysis. For example, the end user can use the microphone to capture a spoken description. Any additional information provided by the user can be used to further analyze the food items. For example, the end user can indicate that the chicken was broiled versus baked, and the object assessment system 102 can take the type of preparation of the chicken into account when determining the nutritional values. As would be appreciated by one skilled in the art, these process steps can be completed simultaneously or sequentially. Once the user finishes eating the entire meal or portions of the meal, the actuation mechanism can be engaged once more by "waving" the computing device 104 over the remaining uneaten food from the dish. The automatic processing steps of the image processing module 116 and the artificial intelligence module 118 repeats, and the food consumption data stored by the network based application would be amended to account for items of food which the user did not finish. The dietary application would present the resulting nutritional information to the user based on the amount of food consumed by the user (e.g., the difference in volumes from the starting captured image data and the final captured image data).

Figure 10B:
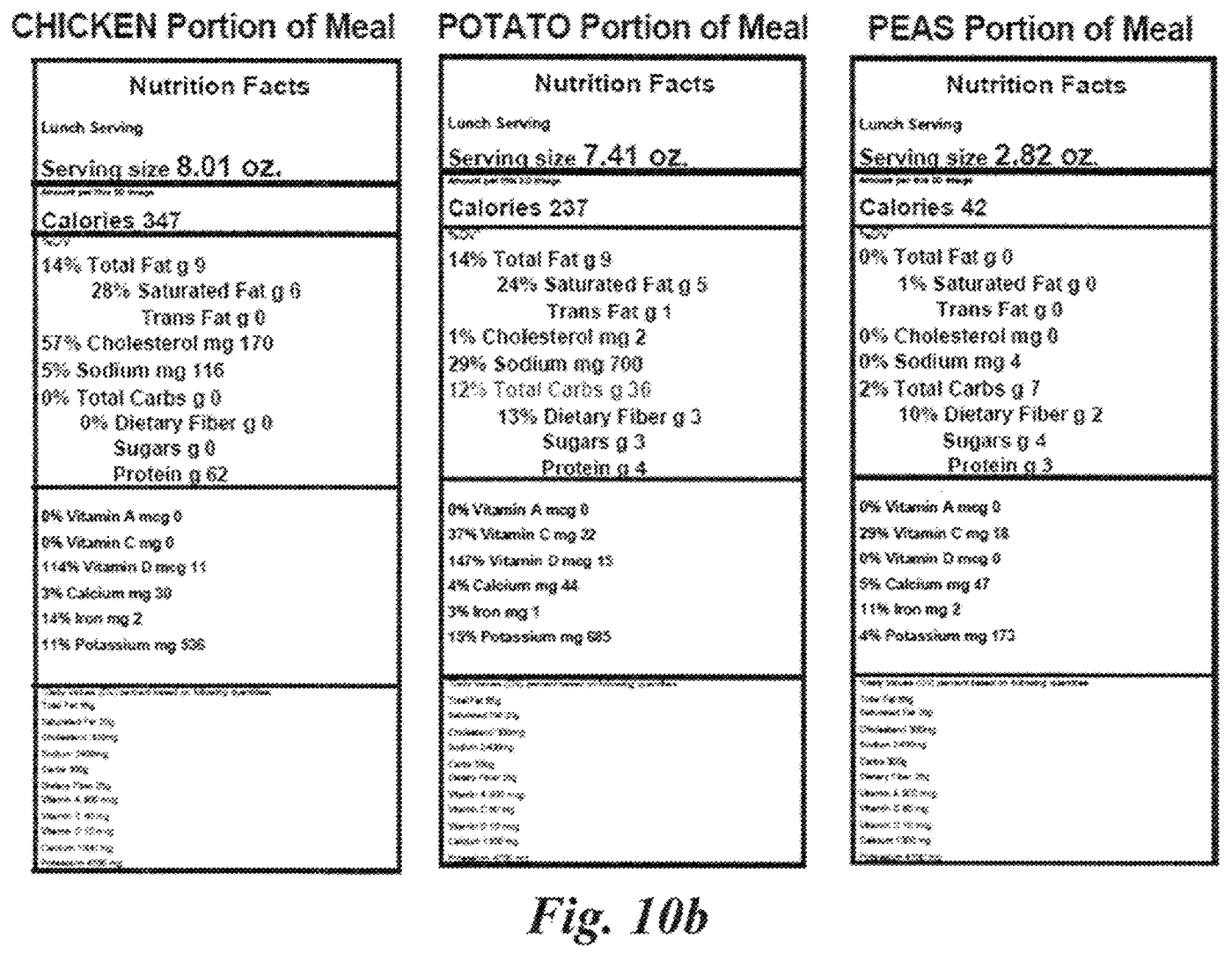

In accordance with an example embodiment of the present invention, the nutritional information can be presented to the end user (e.g., on the dietary tracking application on the user's mobile computing device). FIGS. 10a and 10b depicts example illustrations of the nutritional values for the meal depicted in FIG. 9. In particular, the present invention captures an image of the entire meal with a single capture of image data of the entire plate within the field of view by the image sensor(s) 102 for and instantly produces a nutritional food label for the entire meal (e.g., the combined nutritional information for all of the food items). Without requiring another image capture, the user can then scroll on the computing device 104, 124 to see the segmented or automatically separated nutritional food labels of the individual food items that comprise the entire meal, as depicted in FIG. 10b. The individual nutritional food labels can include the actual weight for each of the food items. In particular, as shown in FIG. 10b, each of the separate food items (e.g., peas, chicken, mashed potatoes) of the meal in FIG. 9 can have a separate nutritional table showing all of the nutritional values for the consumed food items. In accordance with an example embodiment of the present invention, the nutritional food labels can be created based on a volume of food consumed by the user (e.g., using the before and after image captures). As would be appreciated one skilled in the art, any combination of data related to a user's health and/or diet can be presented to the user. For example, a diabetic user can be notified that they have exceeded their desired daily carbohydrate/sugar/other nutrition limits and as well as the ratios of fats to carbohydrates to sodium etc. Similarly, the system can take into consideration from data logged to user's account of their physical activity before and after the meal. For example, if a user exercised before the meal, the system can indicate that the user can have additional calories during their next meal.

In accordance with an example embodiment of the present invention, the dietary application can be a network based application that receives, processes, synthesizes, and displays diet information based on calculations performed with image data sent from the computing device 104 in conjunction with data retrieved from a plurality of public and private databases (e.g., system storage 114). The network based application aides the user in gathering, tracking, and logging information pertaining to his or her diet. The network based application can also include a user account, a graphical user interface, and a suite of application programming interfaces. When the user begins employing the object assessment system 102 and computing device 104, the user first establishes a user account which is linked to that user's device or devices (e.g., the other computing devices 124). When creating the user account, the user inputs information including but not limited to data relevant to that user's health and dietary needs and goals, and food aversions and allergies. The user account automatically stores, processes, and organizes food consumption data collected by that user's device or devices. The graphical user interface enables the user to access, view, input, and alter information pertaining to their user account.

In accordance with an example embodiment of the present invention, the dietary application can include a suite of application programming interfaces utilizing data from multiple databases in conjunction with information gathered by the computing device 104 to facilitate the functions of the object assessment system 102. The suite of application programming interfaces can include a imaging sensor(s) Application Program Interface (API), a three dimensional scanner API, a visual comparison API, a voice recognition API, an auto-segmentation API, a volume to weight API, a nutritive value output API, a 3D print modeling API, a bar code and optical character recognition API, and a food inventory API. The imaging sensor(s) API can use image data output by the imaging sensor(s) 102 of the computing device 104 pertaining to the spectral signatures of items of food in conjunction with a plurality of chemometric algorithms within a Chemometric algorithm database to identify those foods.

Similarly, the three-dimensional scanner API can convert the three-dimensional image data (e.g., the point cloud data) in an .asc or .txt file output by the three-dimensional scanner of the computing device 104 into a file readable by computer assisted design software including but not limited to a .stl or .ply file. The visual comparison API can use the two-dimensional and/or three-dimensional image data captured by the imaging sensor(s) 102 of the computing device 104 in conjunction with a plurality of food image databases (e.g., storage system 114) to identify foods by the two-dimensional or three-dimensional images, as discussed with respect to FIGS. 1-9. The voice recognition API can analyze audio information captured by the microphone of the computing device 104 to identify the foods that are described by the user. In accordance with an example embodiment of the present invention, both the visual comparison API and the voice recognition API are used in case the imaging sensor(s) API is unable to identify the food on the plate.

The auto-segmentation API utilizes the CAD file output by the three-dimensional scanner API can be used in conjunction with the proprietary auto-segmentation algorithms of the object assessment system 102, the spectral signature identifications of the imaging sensor(s) API, and/or two-dimensional or three-dimensional image data to automatically divide a dish containing several different foods into the various different foods which make up the dish, and to calculate the volumes and dimensions of each of the constituent foods of the dish. The volume to weight API uses the food identification data from the chemometric algorithm, data from the 3D scanner, and two-dimensional or three dimensional camera images and cross references these data with databases including a USDA database, an FDA and/or the USDA databases, and a network database, in order to derive the food densities, specific weight calculating constant, and specific calorie calculating constant of those foods. The food densities, specific weight calculating constant, and specific calorie calculating constant are used with the volume of those foods calculated by the auto-segmentation API to calculate the weight and calorie content of the foods which have been scanned. The weight and calorie content of the foods are then stored by the network based application.

The nutritive value output API can use the food identification data from the chemometric algorithm and two-dimensional or three-dimensional image data to cross references the image data with data stored in the databases, including a USDA database, an FDA and/or the USDA databases, and a network database, in order to derive the nutrition information including but not limited to calories, protein, total fat, saturated fat, and fatty acids from the meal, or individual meal components, and makes that information viewable by the user on the graphical user interface, which is formatted similar to a nutrition facts label found on many food packages. The three-dimensional print modeling API can enable a user to export the .stl or .ply CAD file output by the three-dimensional scan API to three-dimensional print modeling software to enable three-dimensional print model of meals. These three-dimensional print models can be used by individual users as models of ideal portion sizes for portion control, or by larger cafeteria or industrial food operations to ensure adequate food production and to design ideal packaging for that food. The bar code and optical character recognition API can use algorithms to analyze an image of a universal product code (UPC) or ingredients list captured by the camera of the computing device 104 to automatically import nutritive value information for that food to the nutritive value API, and to identify and warn the user of possible allergens or food aversion conflicts. The bar code and optical character recognition API can be used, for example, by a user in a grocery store to quickly and effortlessly scan packaged items on shelves to check for allergens or unhealthy ingredients.

The food inventory API can enable the user to automatically keep track of the amount of food in storage. To use the food inventory API, the user first scans ingredients as they are put into storage, such as when items are first brought home from the grocery store and put into the refrigerator and pantry. This establishes inventory baseline values. Then once a meal has been prepared, it is scanned, and the ingredients in that meal are subtracted from the inventory baseline values. The food inventory API may generate a shopping list with the items and associated amounts required to restore the inventory baseline values. The food inventory API works in conjunction with the GPS beacon to ensure that only ingredients of meals eaten in the vicinity of the inventory are subtracted from inventory baseline values. For instance, if a user returns from the grocery store with sixteen ounces of chicken, and subsequently scans eight ounces of chicken at home after preparing a home cooked meal, and then eight ounces of chicken at a restaurant while eating out, then only the eight ounces of chicken scanned at home will be subtracted from the inventory baseline value of chicken. The food inventory may also be used by restaurants or cafeterias to manage inventory.

Figure 11:
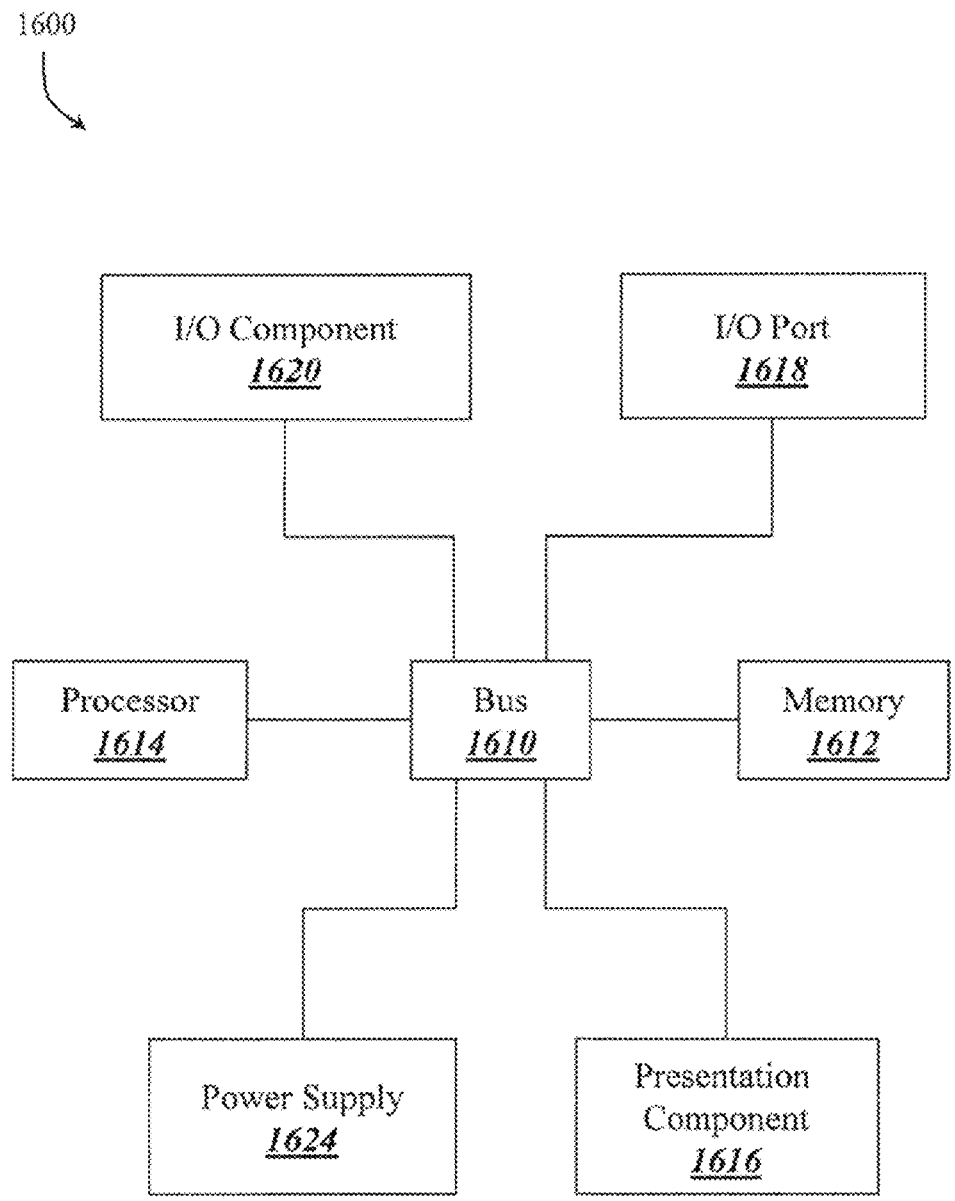
FIG. 11 is a diagrammatic illustration of a high level architecture for implementing system and processes in accordance with aspects of the present invention.

Any suitable computing device can be used to implement the computing devices 102, 104 and methods/functionality described herein and be converted to a specific system for performing the operations and features described herein through modification of hardware, software, and firmware, in a manner significantly more than mere execution of software on a generic computing device, as would be appreciated by those of skill in the art. One illustrative example of such a computing device 1600 is depicted in FIG. 11. The computing device 1600 is merely an illustrative example of a suitable computing environment and in no way limits the scope of the present invention. A "computing device," as represented by FIG. 11, can include a "workstation," a "server," a "laptop," a "desktop," a "hand-held device," a "mobile device," a "tablet computer," or other computing devices, as would be understood by those of skill in the art. Given that the computing device 1600 is depicted for illustrative purposes, embodiments of the present invention may utilize any number of computing devices 1600 in any number of different ways to implement a single embodiment of the present invention. Accordingly, embodiments of the present invention are not limited to a single computing device 1600, as would be appreciated by one with skill in the art, nor are they limited to a single type of implementation or configuration of the example computing device 1600.

The computing device 1600 can include a bus 1610 that can be coupled to one or more of the following illustrative components, directly or indirectly: a memory 1612, one or more processors 1614, one or more presentation components 1616, input/output ports 1618, input/output components 1620, and a power supply 1624. One of skill in the art will appreciate that the bus 1610 can include one or more busses, such as an address bus, a data bus, or any combination thereof. One of skill in the art additionally will appreciate that, depending on the intended applications and uses of a particular embodiment, multiple of these components can be implemented by a single device. Similarly, in some instances, a single component can be implemented by multiple devices. As such, FIG. 11 is merely illustrative of an exemplary computing device that can be used to implement one or more embodiments of the present invention, and in no way limits the invention.

The computing device 1600 can include or interact with a variety of computer-readable media. For example, computer-readable media can include Random Access Memory (RAM); Read Only Memory (ROM); Electronically Erasable Programmable Read Only Memory (EEPROM); flash memory or other memory technologies; CDROM, digital versatile disks (DVD) or other optical or holographic media; magnetic cassettes, magnetic tape, magnetic disk storage or other magnetic storage devices that can be used to encode information and can be accessed by the computing device 1600.

The memory 1612 can include computer-storage media in the form of volatile and/or nonvolatile memory. The memory 1612 may be removable, non-removable, or any combination thereof. Exemplary hardware devices are devices such as hard drives, solid-state memory, optical-disc drives, and the like. The computing device 1600 can include one or more processors that read data from components such as the memory 1612, the various I/O components 1616, etc. Presentation component(s) 1616 present data indications to a user or other device. Exemplary presentation components include a display device, speaker, printing component, vibrating component, etc.

The I/O ports 1618 can enable the computing device 1600 to be logically coupled to other devices, such as I/O components 1620. Some of the I/O components 1620 can be built into the computing device 1600. Examples of such I/O components 1620 include a microphone, joystick, recording device, game pad, satellite dish, scanner, printer, wireless device, networking device, and the like.

As utilized herein, the terms "comprises" and "comprising" are intended to be construed as being inclusive, not exclusive. As utilized herein, the terms "exemplary", "example", and "illustrative", are intended to mean "serving as an example, instance, or illustration" and should not be construed as indicating, or not indicating, a preferred or advantageous configuration relative to other configurations. As utilized herein, the terms "about" and "approximately" are intended to cover variations that may existing in the upper and lower limits of the ranges of subjective or objective values, such as variations in properties, parameters, sizes, and dimensions. In one non-limiting example, the terms "about" and "approximately" mean at, or plus 10 percent or less, or minus 10 percent or less. In one non-limiting example, the terms "about" and "approximately" mean sufficiently close to be deemed by one of skill in the art in the relevant field to be included. As utilized herein, the term "substantially" refers to the complete or nearly complete extend or degree of an action, characteristic, property, state, structure, item, or result, as would be appreciated by one of skill in the art. For example, an object that is "substantially" circular would mean that the object is either completely a circle to mathematically determinable limits, or nearly a circle as would be recognized or understood by one of skill in the art. The exact allowable degree of deviation from absolute completeness may in some instances depend on the specific context. However, in general, the nearness of completion will be so as to have the same overall result as if absolute and total completion were achieved or obtained. The use of "substantially" is equally applicable when utilized in a negative connotation to refer to the complete or near complete lack of an action, characteristic, property, state, structure, item, or result, as would be appreciated by one of skill in the art.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A method for automated detection and processing of a plate of food for nutritional values, the method comprising:
   detecting, by at least one imaging sensor positioned entirely to one side and over objects, edges of the plate of food based on a difference of depth of the plate of food in relation to other objects in a field of view in the sensor target area, the difference of depth based on a difference of distance quantities from the at least one imaging sensor;
   capturing, by the at least one imaging sensor, a three-dimensional model of the plate of food;
   capturing, by the at least one imaging sensor, image data for the plate of food, the image data comprising a visible light image and at least one near-infrared (NIR) image of the plate of food;
   transforming, by a processor, the image data into a composite image, the composite image mimicking a single image taken by a single sensor;
   identifying, by a processor, a food item that corresponds to the composite image;
   transforming, by a processor, the three-dimensional model of the identified food item into a volume for the identified food item; and
   calculating, by a processor, dietary information of the identified food item based on the volume of the food item.

2. The method of claim 1, further comprising:
   determining an initial volume of the identified food item;
   determining a final volume of the identified food item; and
   calculating a change in volume of the identified food item based on a difference of the initial volume of the identified food item and the final volume of the identified food item.

3. The method of claim 2, further comprising:
   obtaining, from a database, dietary information for the identified food item; and
   calculating dietary content of the change in volume of the identified food item.

4. The method of claim 1, further comprising illuminating the plate of food by an LED array and obtaining reflected image data at wavelengths of 745 nm, 810 nm, 940 nm, 970 nm, and/or 1050 nm, and correlating the reflected image data to characteristic food elements.

5. The method of claim 1, wherein the volume and a weight for the identified food item can be calculated in relation to the visible light image and the at least one near-infrared (NIR) image.

6. A method for automated detection and processing of one or more objects in a target area, the method comprising:
 detecting, by at least one sensor, edges of the target area based on a difference of depth of the target area in relation to other objects in a field of view, the difference of depth based on a difference of distance quantities from the at least one sensor;
 capturing, by the at least one sensor, a three-dimensional model of the one or more objects within the target area;
 capturing, by the at least one sensor, image data for the one or more objects, the image data comprising an RGB separated elements or vectors from visible image and a plurality of near infrared vectors for specific wavelengths extracted from the image data of reflected light from the one or more objects;
 transforming, by an image processing module, the image data into a composite image, the composite image mimicking a single image taken by a single sensor;
 identifying, by the image processing module, at least one object of the one or more objects that corresponds to color pixels of the composite image;
 determining, by the image processing module, a volume of space for each pixel in the three-dimensional model based on a depth of pixels;
 transforming, by the image processing module, the volume of space for each pixel for each identified at least one object into a volumetric value for the at least one object; and
 summing, by the image processing module, volumetric values of each of the color pixels of the identified at least one object in the composite image to calculate a total volume of the at least one object.

7. A system, comprising:
 a digital camera comprising:
  at least one image sensor, the digital camera configured to transform captured visible light in a spectrum range and Near Infrared (NIR) light in a spectrum range into captured light voltage; and
  at least one image processing module that transforms the captured light voltage into three-dimensional (3D) image data; and
  a recording device that records the 3D image data;
  wherein the digital camera captures and records at least two different and non-overlapping subsets of light spectrum ranges within the NIR spectrum range and does not record gaps of light spectrum ranges between the non-overlapping subsets of light spectrum ranges;
 an image processing engine configured to:
  analyze the captured and recorded captured light voltage to identify one or more objects;
  determine volumetric data for the one or more objects at a given period of time based on the recorded three-dimensional image data; and
  obtain characteristic information data, from one or more databases, for the identified one or more objects; and
 a display device for outputting the volumetric data and the characteristic information data for the one or more objects.

8. The system of claim 7, wherein:
 the visible light is captured in the spectrum range of 400 nm to 700 nm; and
 the NIR light is captured in the spectrum range of 700 nm to 1050 nm.

9. The system of claim 7, wherein the at least one image sensor further comprises:
 a three-dimensional scanner configured to capture three-dimensional point cloud data of the one or more objects;
 a digital NIR camera with a visible light blocking filter configured to capture light voltage for the one or more objects; and
 an RGB digital camera configured to capture two-dimensional or three-dimensional image data for the one or more objects.

10. The system of claim 9, wherein the digital NIR camera captures a series of two or more images for the at least two different and non-overlapping subsets of light spectrum ranges by cycling one at a time through an array of NIR LEDs.

11. The system of claim 7, wherein the captured light voltage is used to identify one or more sub-objects of the one or more objects.

12. The system of claim 11, wherein the identified one or more sub-objects of the one or more objects are separated and the characteristic information data for each of the one or more sub-objects is obtained from the one or more databases.

13. The system of claim 9, wherein an artificial intelligence engine identifies at least one predefined primitive and triggers the RGB digital camera and the digital NIR camera directed at the at least one predefined primitive.

14. The system of claim 7, wherein the at least one image processing module is configured to use three-dimensional point cloud data of the one or more objects to determine a range from the at least one image sensor to the one or more objects, to determine a surface area of the one or more objects, and calculate a size and shape of the one or more objects using a time of flight and the surface area without use of a fiduciary reference token.

15. The system of claim 14, wherein the time of flight and the surface area of the one or more objects are determined by calculating a number of pixels in a field of view of the three-dimensional point cloud data.

16. An object assessment system, the system comprising:
 an imaging sensor application program interface (API) configured to capture and store visual spectral range image data and near infrared spectral image data of one or more objects;
 a three-dimensional scanner API configured to capture and store three dimensional image data of the one or more objects;
 a visual comparison API configured to identify the one or more objects based on the captured visual spectral range image data and near infrared spectral image data; and
 an auto-segmentation API configured to separate each of the one or more objects based on identification by the visual comparison API and calculate a volume for each of the separate one or more objects based on the three-dimensional image data.

17. The system of claim 16, wherein the one or more objects are one or more food items in a meal.

18. The system of claim 17, further comprising a volume and weight API configured to cross-reference the identified one or more objects with a remote database to determine nutritive values of the one or more objects.

19. The system of claim 18, further comprising a nutritive value output API configured to output nutritional information for each of the one or more objects based on the nutritive values.

20. The system of claim 16, wherein the visual comparison API compares the visual spectral range image data and near infrared spectral image data to predetermined image data values stored in a database.

21. The system of claim 16, further comprising a bar code and optical character recognition API configured to analyze a universal product code (UPC) or list of characters to obtain additional information for the system.

* * * * *